US008663714B2

(12) United States Patent (10) Patent No.: US 8,663,714 B2
Nielsen et al. (45) Date of Patent: Mar. 4, 2014

(54) APPETITE REGULATING DIETARY SUPPLEMENT

(75) Inventors: Soren Vedel Saaby Nielsen, Allerod (DK); Claude Teisen-Simony, Frederiksberg (DK)

(73) Assignee: D.xign Limited, Leicester (GB)

( * ) Notice: Subject to any disclaimer, the term of this patent is extended or adjusted under 35 U.S.C. 154(b) by 0 days.

(21) Appl. No.: 13/511,413

(22) PCT Filed: Nov. 26, 2010

(86) PCT No.: PCT/DK2010/050321
§ 371 (c)(1),
(2), (4) Date: Sep. 17, 2012

(87) PCT Pub. No.: WO2011/063817
PCT Pub. Date: Jun. 3, 2011

(65) Prior Publication Data
US 2013/0004601 A1 Jan. 3, 2013

Related U.S. Application Data

(60) Provisional application No. 61/267,494, filed on Dec. 8, 2009.

(30) Foreign Application Priority Data

Nov. 26, 2009 (DK) .................................. 2009 70232

(51) Int. Cl.
*A01N 65/00* (2009.01)
(52) U.S. Cl.
USPC ........................................................ 424/725
(58) Field of Classification Search
None
See application file for complete search history.

(56) References Cited

U.S. PATENT DOCUMENTS

| | | | |
|---|---|---|---|
| 2,930,701 | A | 3/1960 | Merton et al. |
| 2,935,447 | A | 5/1960 | Miller et al. |
| 5,342,643 | A | 8/1994 | Wolf et al. |
| 6,706,697 | B1 | 3/2004 | MacDonald |
| 2002/0037353 | A1 | 3/2002 | Villagran et al. |
| 2002/0068110 | A1 | 6/2002 | Liu et al. |
| 2004/0096479 | A1 | 5/2004 | Levine |
| 2004/0191237 | A1 | 9/2004 | Davidson et al. |
| 2005/0084592 | A1 | 4/2005 | Aldred et al. |
| 2008/0014315 | A1 | 1/2008 | DeLease |
| 2008/0233245 | A1 | 9/2008 | White et al. |

FOREIGN PATENT DOCUMENTS

| | | |
|---|---|---|
| CN | 1126036 A | 7/1996 |
| CN | 101385540 A | 3/2009 |
| EP | 1410722 A1 | 4/2004 |
| GB | 828350 A | 2/1960 |
| WO | 9308704 A1 | 5/1993 |
| WO | WO-2004110175 A1 | 12/2004 |
| WO | 2005016007 A1 | 2/2005 |
| WO | 2005034635 A1 | 4/2005 |
| WO | 2005051407 A1 | 6/2005 |
| WO | 2006124779 A3 | 1/2007 |
| WO | WO-2007101349 A1 | 9/2007 |
| WO | 2008098579 A1 | 8/2008 |
| WO | 2008000475 A3 | 1/2009 |
| WO | 2009008714 A1 | 1/2009 |
| WO | 2009085928 A3 | 9/2009 |
| WO | 2010108494 A1 | 9/2010 |
| WO | 2011063809 A1 | 6/2011 |
| WO | 2011131203 A3 | 9/2012 |

OTHER PUBLICATIONS

Brownlee, et al., "Alginate as a Source of Dietary Fiber", Critical Review in Food Science and Nutrition, 2005, pp. 497-510, vol. 45, Taylor & Francis, London, England.
Draget, et al., "Alginic Acid Gels: The Effect Of Alginate Chemical composition And Molecular Weight", Carbohydrate Polymers, 1994, pp. 31-18, vol. 25, Elsevier Science Limited, Great Britain.
Hoad, et al., "In Vivo Imaging of Intragastric Gelation and Its Effect on Satiety in Humans", American Society for Nutritional Sciences, 2004, pp. 2293-2300.
Reinbach, et al., Effects of Capsaicin, Green Tea and CH-19 Sweet Pepper on Appetite and Energy Intake in Humans in Negative and Positive Energy Balance, Jun. 2009, pp. 260-265, Clinical Nutrition, Edinburgh, Scotland.
Tomlin, "The Effect of the Gel-Forming Liquid Fibre on Feeding Behaviour in Man", 1995, pp. 427-436, vol. 74, British Journal of Nutrition.

*Primary Examiner* — Michael Meller
(74) *Attorney, Agent, or Firm* — Gifford, Krass, Sprinkle, Anderson & Citkowski, P.C.

(57) ABSTRACT

A dietary supplement for regulating the appetite of an individual is described. The dietary supplement comprises at least one mechanical satiety regulator, and at least one chemical satiety inducer, and may additionally comprise at least one thermogen, and/or at least one side effect remover. The dietary supplement induces satiety based on a combination of occupying part of the volume of the stomach, inducing sending signals to the brain in respect of satiety. Furthermore the dietary supplement may maintain or increase metabolism and reduce side effects such as the amount of produced flatulence. The dietary supplement may comprise fiber, whey, plant parts from plants e.g. of the genus *Capsicum* and plant parts from a species e.g. of the genus *Mentha*.

7 Claims, 4 Drawing Sheets

A

How hungry are you?

Figure 1:
Figure 1:
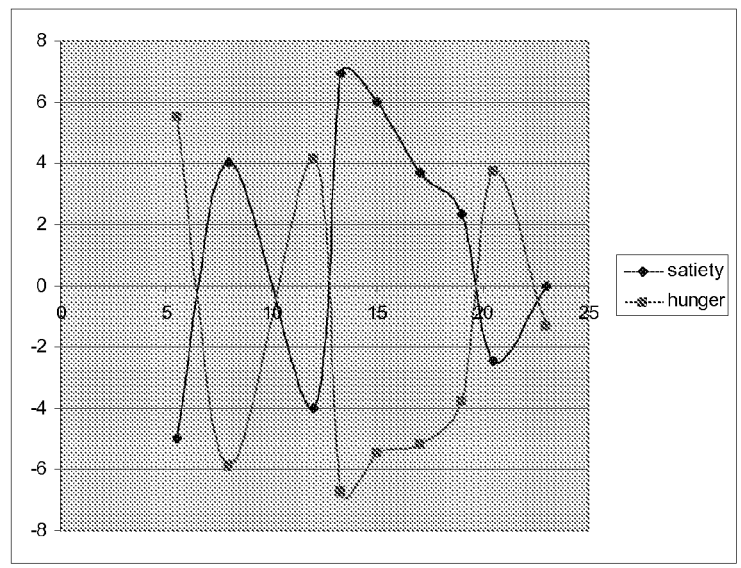

Not at all ←————|————→ Like a wolf

How much could you eat?

Absolutely nothing ←————|————→ Empty the fridge

How satiated do you feel?

Not at all ←————|————→ Extremely

B

A

B

APPETITE REGULATING DIETARY SUPPLEMENT

All patent and non-patent references cited in the application, or in the present application, are also hereby incorporated by reference in their entirety. The application claims the benefit of U.S. 61/267,494 filed on 8 Dec. 2009 and claims priority from Danish patent application no. PA 2009 70232 filed on 26 Nov. 2009.

FIELD OF INVENTION

The present invention relates to a dietary supplement suitable for regulating the appetite of an individual and thereby suitable for obtaining a weight loss of an individual, however, the dietary supplement may also be used i.e. ingested to obtain the feeling of satiety without being used for losing weight of an individual. The dietary supplement or weight control remedy can be used for treatment of overweight and obesity. The dietary supplement can also be used for regulating an individual's feeling of satiety, e.g. where individuals are not in possession of the amounts of food or the type of foods suitable to obtain the feeling of satiety without ingestion of the diary supplement. The dietary supplement comprises a mechanical satiety inducer such as a fibre, and a chemical satiety inducer, and optionally a thermogen and/or a side effect remover.

BACKGROUND OF INVENTION

Weight control, appetite control and/or weight loss is an extremely difficult challenge to some people as well as to the society of many countries. Obesity reduces the life quality of the individuals and imposes expenses to the person and/or to the society in respect of the consequences due to an increased risk of diseases.

Overweight and obesity are increasing problems worldwide and there is a significant and ever increasing market for products and services directed at the problem. Naturally derived and synthetic products aimed at reducing appetite, increasing metabolism, preventing fat uptake are being marketed as are a number of high fibre products aimed at adding "bulk" to today's calorie dense diet.

In extreme cases of obesity surgical methods have been established including gastric restriction by insertion of balloons, removal of part of the stomach, inducing scar tissues in the stomach to make functional stomach volume smaller and gastric bypass operations minimizing the body's ability to absorb fat. In addition non-metabolisable food additives are being developed and marketed as replacements for fat and sugar.

Existing weight control remedies are aimed at reducing appetite by either systemic (hormonal) control of satiety or metabolic rate or by induction of mechanical satiety i.e. low (no) calorie fibre supplements. The systemic approach has some harmful side effects primarily on the cardio-vascular system. The mechanical approach does not present serious side effects but on the other hand do not always result in the desired weight reduction/control as the body adapts to the lower caloric intake by lowering the metabolic rate.

The document CN 1126038 describes a weight-reducing chewing gum. The weight-losing chewing gum is made from 13 Chinese-medicinal components such as raw haw, scabish, raw fleece flower root, white chrysanthemum flower, etc, defatted milk powder or whey powder, gel, proteoglycan, pepper powder, extracted liquid of mint in anhydrous alcohole, essence, hydroxypropyl cellulose and hydroxypropyl methylcellulose, and features its medical functions e.g. of losing weight.

WO 2005/016007 describes a protein enhanced, low carbohydrate wafer having protein material in a concentration of about 26% to about 99% of the wafer. The wafer may contain whey protein.

US 2005/0084592 describes a edible composition comprising at least 1% wt protein and 0.1-5% wt of a biopolymer thickening agent. The composition has a gel strength of at least 10 KPa, and is described to have good satiety effects.

Existing remedies for weight control/loss employ one of 4 strategies
Induction of mechanical satiety
  Fibre products
Inhibition of fat uptake from the intestine
  Synthetic drugs (e.g. orlistat)
  Fibre products
Induction of systemic ("hormonal") satiety
  Synthetic drugs (e.g. sibutramine)
Increasing the metabolic rate
  Both synthetic (amphetamines) and naturally occurring (ephedrine, caffeine) CNS stimulants exist.

The first 3 strategies are aimed at the elimination of calories from the diet, while the fourth strategy is aimed at increasing the metabolism of ingested calories thereby leaving fewer calories for storage of fat. The fourth strategy is also used in combination with diets in order to prevent the lowering of metabolic rate during times of caloric restriction that we are genetically programmed for. The remedies employing the last 3 strategies all have side effects ranging from the embarrassing/impractical (flatulence, diarrea) to the potentially fatal (elevated blood pressure, stroke, ischemia).

Eating behaviour is influenced by hormonal signals in the blood stream (e.g. CCK, Insulin, Glucagon, ghrelin, leptin, GLP-1), by sensory signals (vision, taste, smell), by nerve signals from the stomach reporting fullness via mechanical receptors (baroreceptors).

As human genetic setup is still the same as in our hunter/gatherer ancestors, the body will respond to caloric restriction by lowering the metabolic rate using the ingested energy more efficiently and by storing fat in times of plenty of energy. In order to obtain a weight loss when restricting the intake of calories it is therefore necessary to maintain a metabolic rate comparable to the rate that works under no restriction of energy intake.

The current invention is directed to products that can be sold as a dietary supplement that temporarily reduces gastric volume and which preferrably at the same time induces chemical satiety and thereby reduces the appetite of an individual and that can be administered without the involvement of a physician. Furthermore the product is developed to include ingredients that favour a high metabolic rate in the body of the individual.

SUMMARY OF INVENTION

A dietary supplement for regulating the appetite of an individual is described. The dietary supplement comprises at least one mechanical satiety regulator, and at least one chemical satiety inducer, and optionally at least one thermogen. The dietary supplement may also comprise at least one mechanical satiety regulator, at least one chemical satiety inducer, at least one thermogen, and at least one side effect remover. The dietary supplement induces satiety based on a combination of occupying part of the volume of the stomach, and inducing signals to the brain in respect of satiety. Furthermore the dietary supplement may maintain or increase metabolism and may reduce side effects such as the amount of produced flatulence.

The mechanical satiety regulator is preferably a fibre of the types galactomannan, glucomannan, pectin, arabinoxylan, cellulose, alginate, gellan gum and/or chitosan or a combination hereof. Soluble fibres have a higher capability for absorbing liquids and can thus make a larger volume based on a lower amount of ingested fibre when compared to non-soluble fibres.

The chemical satiety inducer may be obtained from the group of milk protein, protein hydrolysate e.g. legume protein hydrolysate, at least one compound from plant parts from plants of the genus *Capsicum*, from plants of the genera *Brassica* and *Sinapis*, and/or from the plant species *Armoracia rusticana* and/or from the plant species *Solanum tuberosum*.

The thermogen may be plant parts comprising one or more compounds of capsaicins, capsaicinoids, piperins, zingiberins, gingerols, vanillin and/or vanillic acid and/or allyl-isothiocyanat and/or glycosides of these compounds. Especially plant parts from plants of the genus *Capsicum* can be used as a thermogen. Also plant parts or extracts from *Citrus* or green tea may be used.

The side effect remover may be plant parts from a species of the genus *Mentha*. Also plant materials form other plants may be used.

The dietary supplement may be a single product to be ingested or a combination of e.g. a liquid and a non-liquid part to be ingested shortly after each other.

SHORT DESCRIPTION OF THE DRAWINGS

FIG. 1. A. Assessment scales used in a test of the dietary supplement. B. Results obtained from a test of the dietary supplement.

Figure 2:
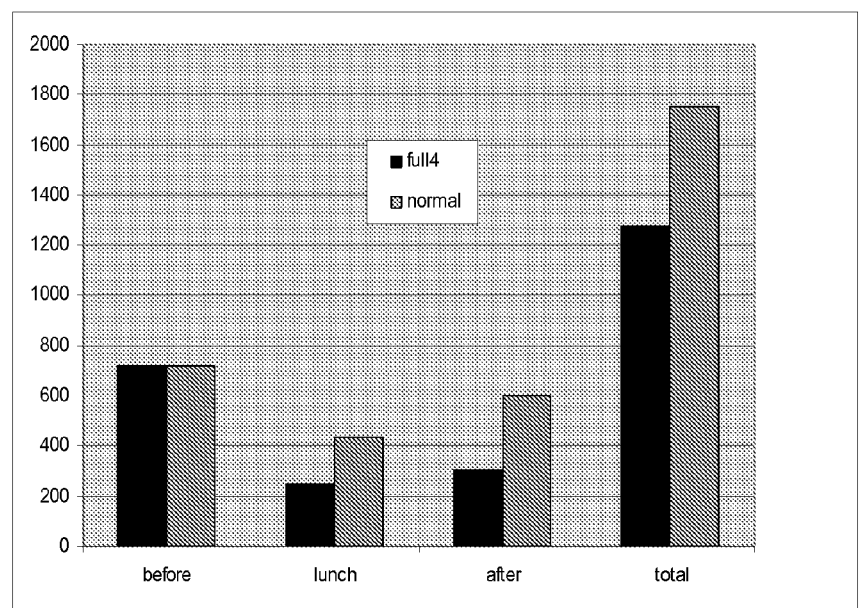

FIG. 2. Intake of calories with and without intake of the dietary supplement.

Figure 3:
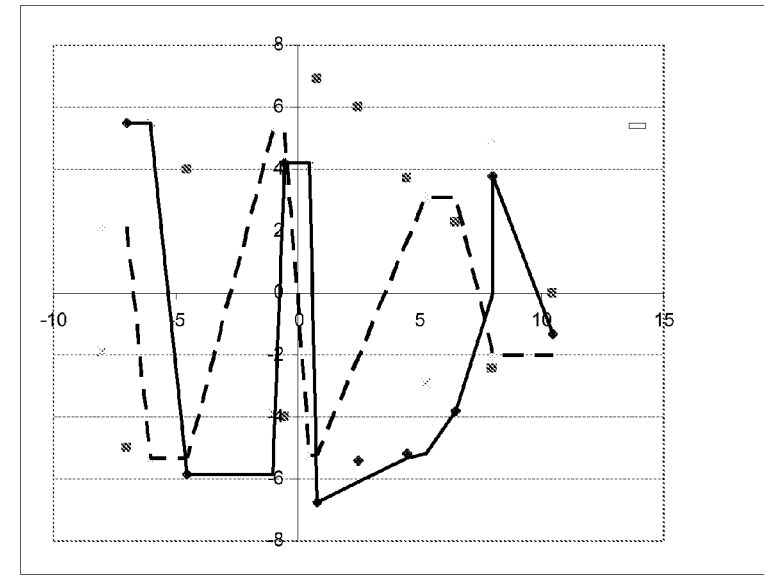
Figure 3:
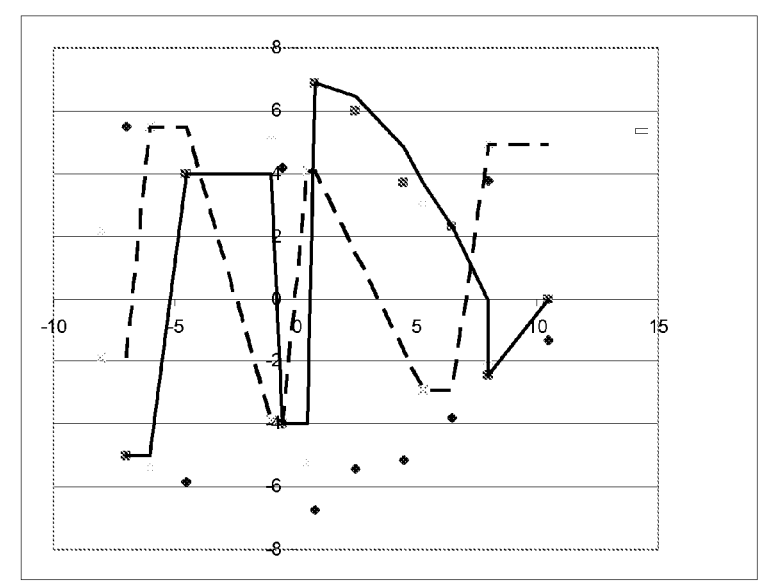

FIG. 3. The feeling of hunger/satiety for individuals with and without intake of the dietary supplement.

Figure 4:
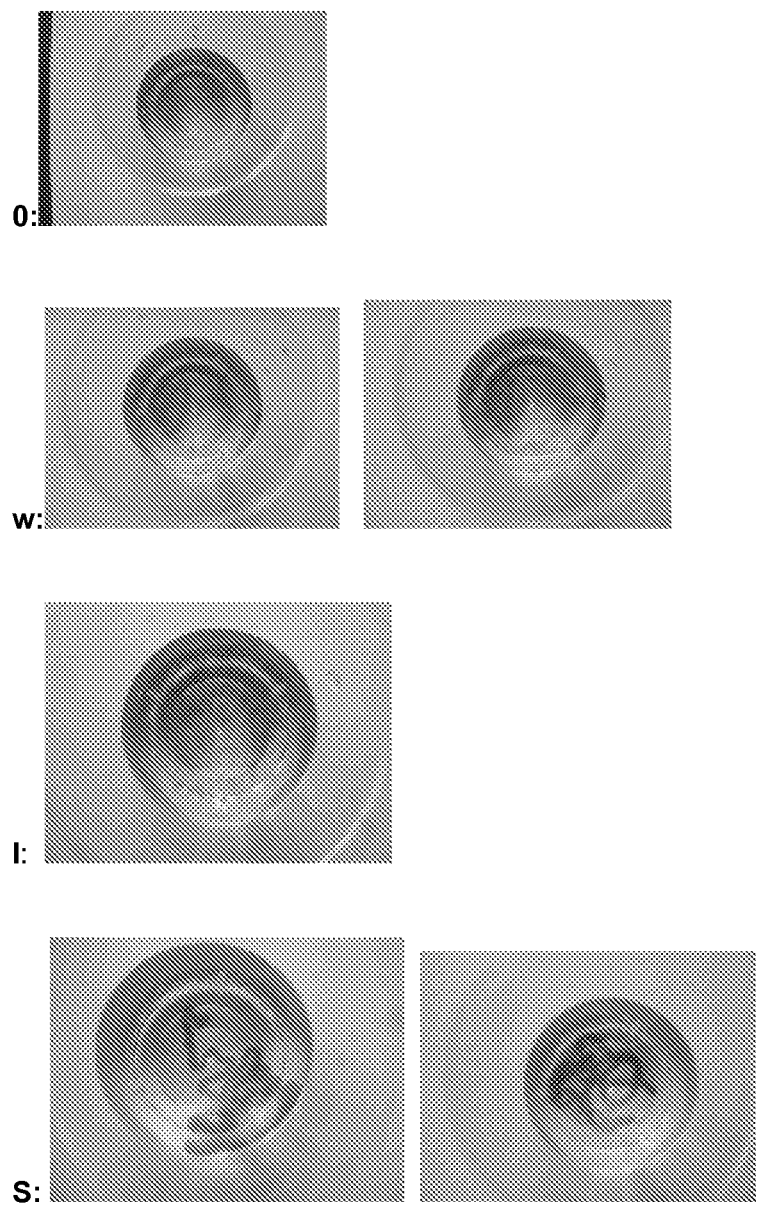

FIG. 4. illustrates the gelation effect of different alginate concentrations.

DEFINITIONS

Alginate or fibre concentration (liquid formulation): When describing the concentration of alginate or other gel-forming fibres, the concentration is meant to be the concentration of the product which is to be ingested. The concentration may also be given in respect of the concentration of alginate in the gel formed in the stomach after ingestion. Thus a 0.125% (w/v) alginate solution corresponds to 125 mg of alginate in 100 ml of liquid e.g. water. When this solution (100 ml) is ingested it turns into a gel of 100 ml when in contact with the gastric acid. 0.125% alginate may also be the concentration of e.g. a liquid food such as a milk product e.g. youghurt, soup, ice cream, or a beverage. When preparing a ready-made meal where e.g. a powder may be mixed with water before ingestion, the concentration of the compounds mentioned herein in the meal is given in respect of the final product that is ingested by the individual unless otherwise specified.

Alginate or fibre concentration (dry formulation): Here the concentration of alginate or other gel-forming fibres in a powder is substantially higher than indicated above, as this formulation (powder, pill, capsule) should be diluted with or be swallowed together with e.g. 100-250 ml of water. In this formulation, the product may suitably comprise from 1-50% (w/w) of alginate. For example this may be in the form of a pill comprising 125 mg alginate which is to be swallowed together with 100 ml of water. In the stomach this will result in the formation of a gel of approximately 100 ml.

Dried redissolved alginate may be added to solid foods in order to make these more satiating. This is done by increasing the volume occupied by solids in the stomach after ingestion of the solid foodstuff containing the dried redissolved alginate gel.

Chemical/systemic/hormonal satiety: satiety mediated via chemical/hormonal signals such as e.g. CCK, GLP, PPY that are induced/activated/excreted in the digestive tract in response to chemical entities in the ingested food or degradation products thereof.

Chemical/systemic/hormonal satiety inducer: an edible or ingestible substance or a compound contained in said substance that is able to induce/activate chemical/hormonal signal as defined above or is able to induce excretion of chemical/hormonal signal as defined above.

Concentration and amount of chemical satiety inducer, of thermogen or of side-effect remover: The concentration of compounds from the groups chemical satiety inducer, thermogen and side-effect remover is meant to be the concentration of the active component in question in a given dose. The amount of chemical satiety inducer in a dose of dietary supplement is often given in absolute terms, i.e. a certain amount given in grams or milligrams of chemical satiety inducer, thermogen or side-effect remover per dose. It is generally acknowledged that individuals require the same absolute amount of these components per dose irrespective of the size of the dose. Thus the ratio between mechanical satiety inducer on one side and the chemical satiety inducer, thermogen and side-effect remover on the other side may vary.

Dose of dietary supplement: The term "dose" is used in respect of the dietary supplement to describe the amount to be ingested by an individual at one time. A dose may by way of example constitute the amount of dietary supplement taken in connection with one meal. However, a dose is not to be understood as a general amount (e.g. 10 g or 100 ml) of the dietary supplement described herein. Rather a dose of dietary supplement is a specific amount which an individual ingest per day or per meal. Hereby doses may be of different weight or volume as different individuals need different amounts of the dietary supplement to replace a portion of a meal e.g. to replace a meal such that 50% of the volume which the meal occupies in the stomach is occupied by the dietary supplement. Grossly speaking every mouthful of a food product comprising the dietary supplement of the invention should generally speaking take up the same volume in the stomach as two mouthfuls of a product without the dietary supplement.

The dose of the dietary supplement can also be the amount of the dietary supplement which is used in food e.g. in a snack food. A dose may correspond to e.g. a volume of 50-600 ml of gel formed in the stomach. The dose depends on the volume of the stomach in an individual and depends on how much the individual wants to lower his or her food consumption. For example, the dietary supplement may be used in an amount corresponding to 30-90% of the volume of the stomach of the individual, such as 40-80%, such as 50-70%, such as 50-60%.

Mechanical satiety: satiety induced by gastric distention.

Mechanical satiety regulator/inducer: the words "regulator" and "inducer" are interchangeable in this context. An edible substance that takes up space in the gastric lumen, thereby resulting in gastric distention and thus satiety.

Side effect: adverse symptoms such as increased gas and abdominal pain induced in the digestive tract as the result of the ingestion of fibre or other ingredients in the appetite regulating remedy.

Side effect remover: a compound or a substance containing a compound that relieves the adverse symptoms such as increased gas and abdominal pain that results from the ingestion of e.g. high fiber.

Thermogen: a compound or a substance containing a compound that uncouples respiration and ATP-generation. Instead the energy is dissipated as heat.

DETAILED DESCRIPTION OF THE INVENTION

A first aspect of the invention relates to a dietary supplement suitable for regulating the appetite of an individual.

The dietary product or dietary supplement may comprise
At least one mechanical satiety regulator, and
At least one chemical satiety inducer
The dietary product may further comprise at least one thermogen, and/or at least one side effect remover.

The at least one chemical satiety inducer may be at least one proteinase inhibitor.

In a preferred embodiment the dietary product or supplement comprises
At least one mechanical satiety regulator,
At least one chemical satiety inducer e.g. at least one proteinase inhibitor and
At least one thermogen, In a preferred embodiment the dietary supplement further comprises at least one side effect remover.

In the dietary supplement the amount of each of the at least one mechanical satiety regulator can be 0.001-5% (w/v or w/w) in a product ready to ingest, such as 0.005-4%, such as 0.01-3%, such as 0.05-2%, such as 0.1-1%. The amount of mechanical satiety inducer in a product ready to ingest varies depending to some degree on the water content of the product.

Products with a high water content include without limitation, soup, icecream, drink, sauce. Products with intermediary water content include without limitation bakery, chips, cookies, muesli and müesli-bars, corn-flakes, minced meat products such as sausages, meat balls, dumplings, pates etc. Products with low water content include without limitation a powder comprising or consisting of the dietary supplement of the invention, a capsule or pill comprising or consisting of the dietary supplement of the invention.

At least one mechanical satiety regulator can be used to fill out part of the stomach. At least one chemical satiety inducer can be used to send signals to the brain about satiety. At least one thermogen can be used to maintain or increase the metabolism of the individual. At least one side effect remover can be used to decrease or prevent e.g. gasses in the stomach or intestine.

By combining ingredients with the four mentioned characteristics an increased effect of the product is obtained. The dietary supplement may be suitable for obtaining a weight loss of an individual. The dietary supplement or weight control remedy can be used for treatment of overweight and obesity, or can be used to regulate appetite in order to reduce caloric intake. In a preferred embodiment the dietary supplement comprises fibre, chemical satiety inducer, thermogen and side effect remover. Any of the fibre, chemical satiety inducer, thermogen and side effect remover mentioned herein may be combined to produce the dietary supplement.

The chemical satiety inducer can also be considered as a chemical, a systemic, or a hormonal satiety regulator, and "the chemical satiety inducer" can be considered to be a "satiety signal inducer", a "chemical satiety signal inducer", or a "chemical satiety regulator".

The term "dietary supplement" is used to denote the product of the invention. The product—dietary product or dietary supplement is an edible or ingestible product. The product has to be ingested or consumed and to enter the stomach of an individual to have the described effect.

In a preferred embodiment the dietary supplement combines ingredients, which together fulfil all the strategies described above i.e. induction of mechanical satiety, inhibition or prevention of fat uptake from the intestine, induction of systemic ("hormonal") satiety and increasing the metabolic rate and preventing intestinal discomfort arising from the use of fibre. As described elsewhere the ingredients may be combined in one product (dietary supplement) or in different products which are to be ingested together or shortly after each other. "Shortly after each other" means ingested within one hour, preferably within half an hour. Especially simultaneous presence of a mechanical satiety regulator and a chemical satiety inducer in the stomach is preferred to make the individual feel satiated.

Mechanical Satiety Regulator

In an embodiment the mechanical satiety regulator is a fibre. A combination of different types of fibres may be present in the dietary supplement. Any fibre mentioned herein may be combined.

The dietary supplement may comprise food fibres that upon hydration swell, thereby making the stomach of an individual full. Fibres suitable to swell and to make a gel are preferred. Food fibres can be of plant or bacterial origin and are thus mostly made of sugars linked in a way so that humans cannot digest them. The fibres bind water by hydrostatic interactions and some of them make gels under certain circumstances.

The fibre of the dietary product may be soluble or insoluble fibres. Fibre intake lowers blood glucose level as well as the level of LDL cholesterol. In addition some fibres bind fat, which then passes through the body without being taken up. The fat-adsorbing fibres are preferred as a part of the dietary product.

Some fibres form gels, while others "only" bind water. Both types of water inclusion adds to the "bulk" of the food and hereby expand the volume of the ingested food. In order to pursue the strategy of mechanical gastric filling, a gelling fibre is preferred. Furthermore, it is preferred that gelation of the fibre is possible in an acid environment such as in the stomach. It is preferred that the fiber forms the gel immediately when it gets into contact with an acid solution. By "immediately" is meant within less than 1 minute, such as less than 30 seconds, e.g. less than 15 seconds, such as less than 10 seconds. Preferably the fiber gelates immediately when being contacted with an acid solution in a container such as in a cup. Also preferably the fiber gelates immediately when getting into contact with the gastric juice of an individuals stomach.

Dietary guidelines from the FDA recommend a total daily intake of 25 g and 38 g of fibre for women and men, respectively. Danish regulations state that a dietary supplement should comprise no less than 10 g of and no more than 30 g of fibre per daily ration. Preferably, the minimal effective daily intake of fibre from a dietary supplement is 14 g. The preferred amount of fibre ingested when ingesting the dietary product can be dependent of the type or types of fibre used within the product. The gelling ability of some fibres makes it possible to obtain a large volume of the product within the stomach thus a low amount of fibre is needed, whereas with fibres with a low or now gelling ability a larger amount of the fibre is needed.

Preferably the daily amount of fibre obtained from the dietary product is preferred to be between 0.5 g and 40 g per day such as between 1 g and 38 g per day. The lower amount can be used to modify eating behaviour—i.e. make people eat less, whereas the high amount of fibre may abolish normal eating. With fibre being able to form a gel a daily intake of fibre by ingesting the dietary product may be in the range 1 g to 20 g, preferred 2-15 g, more preferred 3-10 g. With fibre not being able to form a gel a daily intake of fibre in the dietary product may be 5-50 g, preferred is 10-40 g, more preferred is 15-30 g. With a product comprising both types of fibres i.e. gelling and non-gelling fibres an intake of 2-30 g may be suitable, preferred is 3-25 g, more preferred 4-15 g. However, the daily intake may be dependent on the size of the individual as well as the size of the stomach and the volume of the stomach to be occupied by the dietary product.

Assuming that the dietary product is used for filling up half the volume of the stomach and that the stomach volume should be filled half on at least 3 occasion per day, as well as in respect of 5-6 occasions of "between meals hunger", then 4 g fibre with 5 doses per day i.e. 20 g fibre each day may suffice. This calculation is based on the assumption that the dietary product takes up 250 to 300 ml of stomach volume. For gelling fibres it has been observed that a gel can be formed with 1% fibre in water. This would mean a dose of 3 g fibre. Thus given a minimal dose of for example 14 g of fibre, a total dose size of the dietary product of about 4 g with 5 doses per day can be used. With a density of 1.2 cc/g and a maximal pill size of 0.5 cc this could mean a daily intake of 18-24 pills per day (i.e. for 15 and 20 g daily intake of fibre, respectively) if the pills consist of pure fibre. Depending on the source and nature (i.e. viscosity) of the fibre, gels may be formed with as little as 0.125% fibre, meaning that the formation of 300 ml of gel will only require 375 mg of fibre. Thus filling up the stomach half on 6 daily occasions would only require the daily dose of fibre to be about 2.5 g.

The fibre of the dietary supplement may be a fat binding fibre such as fibre from psyllium seeds, which are also suitable for binding water and for binding cholesterol.

The different types of fibres used in the dietary supplement are further described below.

In an embodiment the fibre of the dietary supplement is a plant fibre and/or an algae fibre. When being a combination of two or more types of fibres, any ratio of the different fibres may be used. For example at least 50% of the fibres of the dietary supplement may be algae fibres.

In another embodiment the fibre may be selected from the group of galactomannan, glucomannan, pectin, arabinoxylan, cellulose, alginate, and/or chitosan.

Preferred are natural fibres. Natural fibres are expected not to hamper the individual ingesting the dietary supplement. More preferred are the fibres mentioned herein as alginate, galactomannans, glucomannans and pectin. These fibres have gelling properties. The mechanical satiety when using gelling fibres is preferably obtained due to the formation of gel in the stomach of an individual. More preferred are alginate, galactomannans, and glucomannans.

In an embodiment the galactomannan to be incorporated in the dietary supplement is selected from the group of fenugreek gum, guar gum, tara gum, and/or locust bean gum (carob gum).

Galactomannan thickens/swells 5-8 times more than starch in food. Galactomannan hydrates without "fish eyes"—i.e. leaves no dry powder in the middle of hydrated particles. Preferably if galactomannan is used in the dietary supplement, this is mixed with other fibres in the dietary product. The gelforming characteristics of the galactomannan are improved when the fibre is mixed other gel forming fibres. Dependent on the concentration galactomannan may not form gels by itself, but does when mixed with gel forming polymers such as pectin or alginate, and make gels more firm and flexible. A combination of galactomannan and alginate is preferred to obtain a gel forming mix of fibres and to obtain a firm and flexible gel.

One gram of the soluble polysaccharide glucomannan can absorb up to 200 ml of water, hereby making it a preferred fibre. Desterification of the glucomannan makes it a better gelation agent, deesterified glucomannan is thus a preferred characteristic of this type of fibre.

Galactomannan may be obtained by using plant parts of *Trigonelle foenumgraecum, Cyamopsis tetragonolobus, Caesalpinia spinosa, Ceratonia siliqua*, and/or plant parts of plant belonging to the family Fabaceae such as Alfalfa (*Medicago sativa*), clover (*Trifolium* species), peas (*Pisum sativum*), beans (species of *Phaseolus, Vicia, Vigna, Cicer, Lathyrus, Lablab, Psophocarpus, Cajanus, Stizolobium, Cyamopsis, Canavalia, Macrotyloma, Erythrina*), lentils (*Lens culinaris*), lupins (*Lupinus* species), mesquite (*Prosopis* species), carob (*Ceratonia siliqua*), soy (*Glycine max*), and/or peanut (*Arachis hypogaea*).

Plant parts may be obtained from beans selected from the group of *Vicia faba* (broad beans, known in the US as fava beans), *Vigna Aconitifolia* (Moth bean), *Vigna Angularis* (azuki bean), *Vigna mungo* (urad bean), *Vigna radiata* (mung bean), *Vigna umbellatta* (ricebean), *Vigna unguiculata* (cowpea—includes the black-eyed pea, yardlong bean and others), *Cicer arietinum* (chickpea also known as the garbanzo bean), *Pisum sativum* (pea), *Lathyrus sativus* (Indian pea), *Lathyrus tuberosus* (Tuberous pea), *Lens culinaris* (lentil), *Lablab purpureus* (hyacinth bean), *Phaseolus acutifolius* (tepary bean), *Phaseolus coccineus* (runner bean), *Phaseolus lunatus* (lima bean), *Phaseolus vulgaris* (common bean, includes the pinto bean, kidney bean, caparrones, and many others), *Glycine max* (soybean), *Psophocarpus tetragonolobus* (winged bean), *Cajanus cajan* (pigeon pea), *Stizolobium* spp (velvet bean), *Cyamopsis tetragonoloba* (guar), *Canavalia ensiformis* (jack bean), *Canavalia gladiata* (sword bean), *Macrotyloma uniflorum* (horse gram), *Lupinus mutabilis* (tarwi), *Lupinus albus* (lupini bean), and/or *Erythrina herbacea* (Coral bean)

The *Trifolium* species is preferably *Trifolium repens*.

The bean is preferably *Phaseolus vulgaris*.

In an embodiment the glucomannan can be obtained from a plant selected from the group of *Aloe* genus and/or *Amorphophallus* and/or *Phaseolus* spp.

The *Phaseolus* spp is preferably *Phaseolus aureus*.

Of the plant material to be used in the dietary supplement the Aloe species may be selected from the group of plant species *Aloe vera* (syn *A. barbadensis, Aloe indica, Aloe perfoliata* and *A. vulgaris*), *Aloe arborescens, Aloe aristata, Aloe dichotoma, Aloe nyeriensis, Aloe variegata, Aloe barbadensis, Aloe wildii*. Preferred is plant material from *Aloe vera*.

A preferred species of the *Amorphophallus* species is *Amorphophallus konjac*.

Plant parts from dicotyledons can be selected from species belonging to the family Fabaceae and/or Araceae.

The plants belonging to the family Fabaceae can be selected from the species *Medicago sativa, Trifolium species, Pisum sativum, Lens culinaris, Lupinus* species, *Prosopis* species, *Ceratonia siliqua, Glycine max, Arachis hypogaea, Vica faba, Vigna Aconitifolia, Vigna Angularis, Vigna mungo, Vigna radiata, Vigna umbellatta, Vigna unguiculata, Cicer arietinum, Pisum sativum, Lathyrus sativus, Lathyrus tubero-

*sus, Lens culinaris, Lablab purpureus, Phaseolus acutifolius, Phaseolus coccineus, Phaseolus lunatus, Phaseolus vulgaris, Glycine max, Psophocarpus tetragonolobus, Cajanus cajan, Stizolobium* spp, *Cyamopsis tetragonoloba, Canavalia ensiformis, Canavalia gladiata, Macrotyloma uniflorum, Lupinus mutabilis, Lupinus albus*, and/or *Erythrina herbacea*.

In an embodiment pectin used in the dietary supplement can be obtained from the group of plants of sugar beets (*Beta vulgaris*), carrot (*Daucus carota*), apple (*Malus domestica*), apricot (*Prunus armeniaca*), quince (*Cyclonia oblonga*), plum (*Prunus* species), gooseberries (*Ribes uva-crispa*), and/or orange (*Citrus×sinensis*) and or lime (*Citrus×aurantia, Citrus×hystrix*) and/or lemon (*Citrus limon*). Preferred is pectin from apple, citrus species, and/or sugarbeet.

Pectins gel at low concentrations (0.3-0.7%). A preferred content of pectins of any type or combination of any types of pectins mentioned herein is 0.1-1%, more preferred 0.3-0.7%, further preferred 0.4-0.6%. Preferably the dietary supplement is heated before intake to make the pectins form a gel. The dietary supplement can be heated when being produced i.e. before sale or it can be heated by the consumer before intake.

The speed of gelation of the pectins depends on the degree of methylation. Low methylation corresponds to slow gelation and high methylation corresponds to fast gelation. Once formed HM-gels do not remelt as opposed to LM gels. HM is highly metoxylated pectins, LM is low metoxylated pectins. The formation of HM-gels is preferred for the dietary supplement.

Preferably the dietary supplement is brought to a pH below 3 to make the pectins form a gel and/or divalent cat-ions (e.g. Ca) can be included in the dietary supplement to improve the gel forming properties of the pectins. Preferred is Ca-gelation with LM pectin and/or HM pectin with a blockwise methylation.

The dietary supplement may include plant parts of the *Prunus* species selected from *Prunus cerasus, Prunus persica, Prunus dulcis*.

In an embodiment the fibre of the dietary supplement can be arabinoxylan. Depending on the exact structure, arabinoxylans can be either soluble or insoluble. Preferably the arabinoxylans used for the dietary supplement are soluble arabinoxylans.

The function of the arabinoxylans in the dietary supplement is not to form gels but to bind water.

The arabinoxylan of the dietary supplement may be obtained from one or more dicotyledonous plants.

The dietary supplement may include plant parts from dicotyledonous plants belonging to the genus *Plantago*. Preferred species are *Plantago major, Plantago psyllium* and *Plantago ispaghula*.

In an embodiment the fibre of the dietary supplement may be alginate.

The alginate may be obtained from algae of the group of families of Akkesiphycaceae, Alariaceae, Chordaceae, Costariaceae, Fucaceae, Laminariaceae, Lessoniaceae, and/or Pseudochordaceae. Preferred are alginate from Laminariaceae, Fucaceae, and Lessoniaceae.

Preferably the salts of alginates are used in the dietary supplement as these salts are soluble in water whereas the alginates themselves are less soluble or insoluble in water. Alginates form gels with divalent cat-ions (e.g. Ca) or in acidic environments.

Alginate is a preferred source of fibre in the dietary supplement as these can form gels at low concentrations.

The alginate of the dietary supplement may be obtained from the group of *Macrocystis pyrifera, Ascophyllum nodosum, Laminaria hyperborean, Laminaria digitata*, and/or *Laminaria japonica*.

The alginate of the dietary supplement may also be obtained from the group of bacterial genera belonging to *Pseudomonas* and/or *Azotobacter*. Preferred is alginate obtained from *Pseudomonas aeruginosa*.

The alginate of the dietary supplement may be obtained from *Azotobacter vinelandii*, and/or *Azotobacter chroococcum*.

A preferred amount of fibre in the dietary supplement i.e. of the dietary supplement which an individual is about to ingest is 0.01 to 3% when using alginate. More preferred is 0.05-1% of alginate.

A preferred amount of fibre in the dietary supplement i.e. of the dietary supplement in a dose which an individual is about to ingest is 100-1500 mg when using alginate, such as 100-500, for example 100-200 mg. More preferred is 125-1000 mg of alginate.

125 mg of alginate dissolved in 100 ml of liquid can make 100 ml of gel in acid such as in gastric juice. Hereby a low amount of fibre is suitable to produce a high volume of dietary supplement when ingested.

In a preferred embodiment the dietary supplement when being based on alginate is mixed with a liquid e.g. water, and heated or preferably boiled to dissolve the alginate. When heated the dietary supplement is ready to be ingested.

The cellulose of the dietary supplement may be obtained from wood pulp, grass e.g. straw, cotton and/or microbial fermentation of e.g. xylose.

Humans cannot digest cellulose and it is often referred to as 'dietary fibre' or 'roughage' and acts as a hydrophilic bulking agent for feces. About 33 percent of all plant matter is cellulose, although the cellulose content of cotton is 90 percent and of wood it is 50 percent. Cellulose has no taste, is odourless, is hydrophilic, is insoluble in water and in most organic solvents, it is chiral and it is biodegradable. Cellulose is insoluble and binds water. Due to the capability of cellulose to bind water and that it has no taste and is odourless, it may be a preferred fibre of the dietary supplement.

The chitosan of the dietary supplement may be obtained by deacetylation of chitin obtained from an animal of the subphylum Crustacea and/or obtained from a fungus and/or from a transgenic organism.

Chitin is insoluble and binds water as well as some nutrients. Chitin, which is the polymer making up the skeleton of shellfish such as lobsters, shrimps and crayfish can also be used in the product. Using chitosan as the fibre in the dietary product addresses two strategies namely mechanical restriction of the volume of the digestive tract and at the same time binding ingested fat and thus preventing fat uptake and metabolism.

Chitosan to be used in the dietary supplement can be derived from chitin from crabs, lobsters, shrimps, crayfish, krill and/or barnacles.

Chitin from crabs can be obtained from all crabs, preferred crabs are *Hemigraphus oregonensis, Pachygraphus crassipes* (shore crabs), *Pugettia producta, Loxorhynchus grandis, Loxorhynchus crispatus* (spider crabs), *Pinnixa* spp. (pea crabs), *Cancer* spp. (cancer crabs), *Randallia* spp. (globe crabs). Further crabs, but less preferred are *Corystes cassivelaunus, Liocarcinus vernalis, Atelecyclus rotundatus, Geocarcinus quadratus, Stenorhynchus seticornis, Grapsus grapsus, Thia scutellata, Macrocheira kaempferi, Ocypode quadrata, Uca pugnax, Lyreidus tridentatus*, and *Hepatus epheliticus*.

Chitin from lobsters can be obtained from e.g. *Homarinus capensis* (Cape lobster), *Homarus americanus* (American lobster), *Homarus gammarus* (European lobster), *Metanephrops andamanicus* (Andaman lobster), *Metanephrops australiensis* (Australian scampi), *Metanephrops binghami* (Caribbean lobster), *Metanephrops boschmai* (bight lobster), *Metanephrops challengeri* (New Zealand scampi), *Metanephrops japonicus* (Japanese lobster), *Nephrops norvegicus* (Norway lobster), and *Nephropsis aculeata* (Florida lobsterette).

Chitin from shrimps can be obtained from *Alpheus* spp. *Heptacarpus* spp. *Calianassa* spp. and the species *Pandalus platyceros, Acetes japonicus, Palaemon adspersus, Pleoticus muelleri, Artemesia longinaris, Xiphopenaeus kroyeri, Penaeus aztecus, Penaeus merguiensis, Aristeus antennatus, Metapaeneus endeavouri, Penaeus esculentus, Penaeus californiensis, Heterocarpus reedi, Haliporoides diomedeae, Pandalus borealis, Parapenaeus longirostris, Metapenaeus ensis, Penaeus semisulcatus, Parapenaeopsis atlantica, Metapenaeus affinis, Parapenaeopsis stylifera, Penaeus indicus, Sicyonia brevirostris, Hymenopenaeus triarthrus, Solenocera agassizii, Penaeus latisulcatus, Pleoticus robustus, Penaeus brevirostris, Penaeus chinensis, Parapenaeopsis hungerfordi, Penaeus vannamei, Heterocarpus affinis, Heterocarpus vicarious, Solenocera membranacea, Penaeus setiferus, Penaeus duorarum, Pandalus jordani, Metapaeneus monoceros, Parapenaeopsis sculptilis, Metapenaeopsis barbata, Penaeus kerathurus, Aristaeomorpha foliacea, Penaeus penicillatus, Palaemon serratus, Metapaeneus joyneri, Plesiopenaeus edwardsianus, Penaeus monodon, Parapenaeopsis hardwickii, Penaeus notialis, Palaemon elegans, Metapenaeus eboracensis*, and *Pandalus montagui*.

Preferred chitin is obtained from the shrimps: *Palaemon adspersus, Penaeus esculentus, Pandalus borealis, Penaeus semisulcatus* and/or *Penaeus indicus*.

Chitin obtained from crayfish may be obtained from *Austropotamobius pallipes, Procambarus clarkii, Astacus astacus, Pacifastacus leniusculus, Orconectes limosus, Pacifastacus leniusculus, Procambarus clarkii*, and *Cambarus* spp.

Chitin obtained from krill may be obtained from *Euphausia superba, Euphausia pacifica, Euphausia crystallorophias, E. frigida, E. longirostris, E. triacantha* and *E. vallentini*.

Chitin may be obtained from Barnacles. Preferred is chitosan from *Pollicipes polymerus,*

The chitosan of the dietary supplement may be derived from chitin from a fungus selected from the group of basidiomycetes, ascomycetes, phycomycetes, saccharomycetes.

Chitin obtained from a fungus may be obtained from both multicellular (the mushrooms) and unicellular (yeasts). Preferably chitosan is obtained from transgenic fungi.

The chitosan used in the dietary supplement may be obtained from a transgenic organism selected from the group of transgenic microorganism or from transgenic plants.

Preferably, transgenic plants producing chitin and/or chitosan are crop plants (for example, maize, sorghum, wheat, sunflower, tomato, crucifers, peppers, potato, cotton, rice, soybean, sugarbeet, sugarcane, tobacco, barley, oilseed rape, etc.). Preferred is also a transgenic plant of the monocot plant family including, but not limited to, maize, rice, barley, oats, wheat, sorghum, rye, sugarcane, pineapple, yams, onion, banana, coconut, and dates.

The chitosan to be incorporated in a dietary supplement may be obtained form a transgenic microorganism selected from a fungus of *Aspergillus niger* or *Rhizopus oryza* or from a yeast or from bacterium such as *Escherie coli*.

For genetic engineering to increase chitin and chitosan content, suitable fungal hosts include, but are not limited to, Ascomycetes, Zygomycetes and Deuteromycetes. Suitable genera include, but are not limited to, *Aspergillus, Absidia, Gongronella, Lentinus, Mucor, Phycomyces, Rhizopus, Chrysosporium, Neurospora* and *Trichoderma*. Suitable fungal species include, but are not limited to, *Aspergillus niger, Aspergillus terrreus, Aspergillus nidulans, Aspergillus orzae, Absidia coerulea, Absidia repens, Absidia blakesleeana, Gongronella butleri, Lentinus endodes, Mucor rouxii, Phycomyces blakesleenaus, Rhizopus* spp. *Chrysosporium lucknowense, Neurospora crassa, N. intermedia, Trichoderm reesei* and *Saccharomyces cerevisiae*.

Suitable genera of yeast for genetic engineering of microorganism to improve the production of chitin and chitosan include, but are not limited to, *Saccharomyces, Schizosaccharomyces, Candida, Hansenula, Pichia, Kluyveromyces*, and *Phaffia*. Suitable yeast species include, but are not limited to, *Saccharomyces cerevisiae, Schizosaccharomyces pombe, Candida albicans, Candida guillermondii, Hansenula polymorpha, Pichia pastoris, P. canadensis, Kluyveromyces marxianus* and *Phaffia rhodozyma*.

Chitin could be produced by fermentation of any of the mentioned unicellular fungi or by harvesting naturally grown mushrooms. WO 2006/124779, describes transgenic organism producing chitin and chitosan.

The dietary supplement according described herein may comprise one or more of the fibres galactomannan, glucomannan, pectin, arabinoxylan, alginate, cellulose and/or chitosan. Any type of fibre mentioned herein may be used in the dietary supplement. When using a combination of cellulose and/or chitosan as the fibre source, these fibres may comprise less that 15% (w/w) of the total amount of the fibre. 10% of cellulose and/or chitosan is preferred, this improves rehydration properties of the dietary supplement.

Alginate

Alginate is a preferred compound in the dietary supplement. More preferably, the alginate is sodium alginate, Na-alginate. Alginate, also called algin or alginic acid, is an anionic polysaccharide distributed widely in the cell walls of brown algae, where it, through binding water, forms a viscous gum. In extracted form it absorbs water quickly; it may be capable of absorbing 200-300 times its own weight in water. The alginate used in the dietary supplement man by in the form of filamentous, granular or powdered forms. Preferred is a powder of Na-alginate.

Alginate is a linear copolymer with homopolymeric blocks of (1-4)-linked β-D-mannuronate (M) and C-5 epimer α-L-guluronate (G) residues, covalently linked together in different sequences or blocks. The monomers can appear in homopolymeric blocks of consecutive G-residues (G-blocks), consecutive M-residues (M-blocks), alternating M and G-residues (MG-blocks), or randomly organized blocks.

It has been observed by the inventors that in respect of Na-alginates of a molecular weight of 50,000 to 500,000 the block length or amounts of G-blocks or M-blocks does not influence the required gelling properties when producing a dietary supplement as described herein when the concentration of the Na-alginates was in the range of 0.1 to 0.25%. However, when the concentration of the Na-alginate was below 0.1% such as at 0.0625%, the block structure had an influence of the acid gelation properties, it seems as if a high amount of mannuronic acid residues are more willing to gel at this low concentration.

Suitable alginates have a molecular weight of between 10,000 and 600,000. Any MM-block percentage can be used as shown by the examples. A suitable alginate is an alginate with a molecular weight of between 350,000 and 600,000, preferably with an amount of MM-blocks of 30-55%. Also preferred is an alginate with a molecular weight of between 400,000 and 550,000 and an amount of MM-blocks of 35-50%. Further preferred is an alginate with a molecular weight of between 475,000 and 525,000 and an amount of MM-blocks of 40-45%.

In alternative embodiments, the alginate is of relatively low molecular weight such as in the interval between 10,000 and 350,000, such as between 250,000 and 350,000, such as between 150,000 and 250,000, such as between 50,000 and 150,000. Molecular weights at or below 50,000 are also contemplated such as between 50,000 and 10,000, preferably between 50,000 and 40,000.

The alginate of the dietary supplement may be extracted from seaweed, including the giant kelp Macrocystis pyrifera, Ascophyllum nodosum, and various types of Laminaria. It may also be bacterial alginates produced by one or both of the two bacterial genera *Pseudomonas* and *Azotobacter*.

A preferred amount of fibre in the dietary supplement i.e. of the dietary supplement in a dose which an individual is about to ingest is 100-1500 mg when using alginate, such as 100-500, for example 100-200 mg. More preferred is 125-1000 mg of alginate.

More preferably the amount of alginate in a liquid form of the dietary supplement is 0.05-4% (w/v), such as 0.1-3% (w/v), such as 0.1-2% (w/v), such as 0.125-1% (w/v), such as 0.125-0.5% (w/v), such as 0.125-0.4% (w/v). Preferably the concentration of alginate is 0.1-0.5% (w/v) of a liquid dietary supplement. These percentages refer to the percentage alginate in the liquid part of a product such as a meal. Many meals contain both a liquid phase and a solid or semisolid phase. As an example a sauce or soup typically comprises pieces (e.g. dices, chops, slices) of vegetables, and/or meat or meatballs. The gel-forming alginate will typically not be present inside these solid ingredients.

The concentration of alginate in the gel formed by contact of the supplement with the gastric juice may suitably be 0.001-5% (w/v), such as 0.01-4%, such as 0.05-1%, for example 0.05-0.5%, such as 0.1-0.5%.

Alginate and/or another fibre capable of forming a gel can be dissolved in an amount of liquid e.g. water corresponding to the amount or volume which the gel should occupy in the stomach of an individual. When alginate dissolved in water gets into contact with the acidic gastric juice in the stomach, the alginate forms the gel and this gel has the volume identical to the volume of the alginate containing liquid. The concentration of alginate or another gel-forming fibre in liquid should be as described elsewhere herein. e.g. 100 ml of liquid with a concentration of 0.125% of alginate will form a gel of 100 ml when in contact with the gastric juice.

Dried, Re-dissolved Gel

A preferred embodiment of the invention relates to a dried, re-dissolved gel. A dried, redissolved gel can be manufactured by making a gel from alginate and a divalent cation, re-dissolving the gel by adding an amount of a compound capable of complexing the divalent cation, thereby re-dissolving the gel.

Preferably the gel is washed prior to re-dissolving to remove excess divalent cation. Washing is suitably done in water, such as deionised water.

The divalent cation is preferably selected from the group consisting of calcium and magnesium, more preferably calcium. Calcium can be complexed by a number of compounds in a pH dependent manner. The compounds capable of complexing the calcium are preferably selected from the group consisting of weak organic acids, such as acetic acid, lactic acid, oxalic acid, tartaric acid and citric acid, weak to strong organic acids such as phosphoric acid.

Citric acid and phosphoric acid have the advantage that they are capable of complexing calcium at a pH around neutral but are not capable of complexing calcium at low pH such as the pH of gastric juice. It has surprisingly been found that a dried re-dissolved gel will form the gel again when exposed to gastric juice or a solution with the same pH. Under these conditions, citric acid or phosphoric acid are protonised and lose the ability to bind calcium. The calcium is then liberated and can interact with the alginate to form a gel in the stomach.

Preferably the alginate is initially gelled and redissolved at or around neutral pH.

The redissolved gel can be dried by conventional methods such as Bed drying, Drum drying, Fluidized bed drying, Freeze Drying, Shelf drying, Spray drying, Sunlight drying, by using Commercial food dehydrators, or a Household oven. Preferably the redissolved gel is spray dried or freeze dried.

Following drying, the dried, re-dissolved gel can be crushed into a dry powder using methods generally known in the art. The powder can be formulated into pills, or be encapsulated or be used as powder. The powder has the advantage that it can be included directly into food as illustrated in the recipes in the appended examples.

A chemical satiety inducer as herein described can be included into the dried re-dissolved gel, by dissolving the chemical satiety inducer together with the alginate. To the extent that the thermogen and side effect removers herein described are water-soluble, these can also be included into the gel prior to drying. Thereby a complete dietary supplement can be made.

In general, the amount of divalent cation should be enough to gel substantially the alginate. Similarly, the amount of compound capable of complexing the divalent cation can be determined by titration, so that just enough is added to re-dissolve the gel.

In an alternative embodiment, the components, alginate, divalent cation and compound capable of complexing the divalent cation, can be mixed together in one step and be subjected to drying.

The composition of a typical dried, redissolved gel is:
From 1-10% (w/w) alginate
From 5-25% (w/w) calcium or magnesium salt, preferably $CaCl_2$
From 20-75% (w/w) citric acid or equivalent amount of phosphorous acid
From 0.1-1% (w/w) chemical satiety inducer, preferably whey protein Following drying and powdering, the product can be mixed with dry, encapsulated thermogen and side-effect remover.

Chemical Satiety Inducer

A chemical satiety inducer of a dietary supplement may be obtained from the group of milk protein, protein hydrolysate e.g. legume protein hydrolysate, at least one compound from plant parts from plants of the genus *Capsicum*, from plants of the genera *Brassica* and *Sinapis*, from the plant species *Armoracia rusticana* and/or the plant species *Solanum tuberosum*.

By including a chemical satiety inducer in the dietary supplement together with a mechanical satiety regulator when ingested by an individual, satiety is communicated to the brain chemically as well as mechanically. The signals are integrated in specialised parts of the brain which then control eating behaviour. It is possible that more than one type of signal is required in order to perceive satiety and thus reduce caloric intake.

Whey protein can be used as a chemical satiety inducer. A major component (>20%) of whey protein is a peptide named glycomacropeptide (GMP), which induces the activity of the receptor and of CCK in the stomach. Purified GMP may have a more pronounced effect on satiety than would whole whey. A high level of GMP in the dietary supplement without using purified GMP can be obtained from whey which can be obtained from a source that produces a high level of GMP. This is possible since different races of cows, goats and sheeps produce milk with different levels of GMP. The level of GMP in the milk is also influenced by the season of the year, the fodder and the mother status of the animals i.e. the amount of BMP in whey can be influenced both genetically as well as environmentally. Whey is furthermore a waste product form cheese manufacture.

If whey is used in the dietary supplement it is preferably used to influence the activity of physiological satiety signal and is thus not expected to be required in large amounts. An amount of 0.1 mg to 100 mg whey in the dietary supplement calculated per dose to be ingested can be used. Preferred is 1-50 mg per dose. More preferred is 5-25 mg per dose.

Given as percentage (w/v) of the gel formed in the stomach of an individual after ingestion, the concentration of each of the at least one chemical satiety inducer, thermogen, and side-effect remover in the gel formed by the dietary supplement may be below 0.1% (w/v), such as below 0.09%, such as below 0.08%, such as below 0.07%, such as below 0.06%, such as below 0.05%, such as below 0.04%, such as below 0.03%, such as below 0.02%, such as below 0.01%, such as below 0.005, such as below 0.004, 0.003, 0.002, or 0.001.

On a per dose basis, the amount of each of the at least one chemical satiety inducer, thermogen, and side-effect remover in the dietary supplement which is ready to be ingested may be 0.1-100 mg/dose, such as 1-50 mg/dose, such as 5-25 mg/dose.

In a preferred embodiment the dietary supplement comprises GMP in an amount of 0.01 to 20 mg per dose. More preferred is 0.05 to 5 mg GMP per dose. Further preferred is 0.1 to 2 mg GMP per dose.

Protein hydrolysates from leguminous plants may have an identical effect as GMP as a chemical satiety inducer. The effect may originate from the presence of proteinase inhibitors in the hydrolysates. Also proteinaceous preparations from other plants such as e.g. potato containing proteinase inhibitors can function as satiety inducers by inducing excretion of CCK and/or by inhibiting the degradation of CCK and/or by inhibiting degradation of its receptors. Furthermore long-chained fatty acids such as e.g. conjugated linoleic acid and pinolenic acid may induce CCK and thereby satiety.

Hot spices may influence satiety by providing the food with a more satisfactory taste, although a chemical effect may also be present when using plant parts or spices. Capsaicin affects satiety directly via signals originating in the stomach. The effect on satiety is highest if the capsaicin is eaten i.e. perceived by the body both when the capsaicin is in the mouth and in the stomach. Some people don't like hot food it may therefore be preferred to settle for the stomach effect, i.e. encapsulate the hot spices of the dietary product. By encapsulating hot spices or other compounds having a taste not accepted by some individuals, it is possible for these individuals to ingest an amount of the dietary supplement suitable to obtain an effect of the intake of food/calories.

The whey is preferably used to influence the activity of physiological satiety signal and is thus not expected to be required in large amounts. An amount of 0.1 mg to 100 mg whey in the dietary supplement calculated per dose to be ingested can be used. Preferred is 1-50 mg per dose. More preferred is 5-25 mg per dose.

The gel formed either before ingestion or when a liquid dietary supplement as described herein is contacted with gastric juice may contain protein and/or proteinase inhibitor and/or GMP in an amount of below 5% (w/v), such as below 4%, such as below 3%, such as below 2%, preferably below 1%, such as below 0.8%, such as below 0.6%, such as below 0.4%, such as below 0.2%, such as below 0.1%, such as below 0.09%, such as below 0.08%, such as below 0.07%, such as below 0.06%, such as below 0.05%, such as below 0.04%, such as below 0.03%, such as below 0.02%, such as below 0.01%. The percentage is determined on the basis of the weight of the protein and the volume of the gel formed by the dietary supplement.

Milk protein used in the dietary supplement may be obtained from milk obtained from cows, goats, and/or sheeps.

The milk protein of the dietary supplement may be selected from the group of glucomacropeptide (GMP), α-lactalbumin, β-lactoglobulin, lactoferrin, whey protein concentrate (WPC), and/or whey protein isolate (WPI).

Whey easily dissolves in the stomach and is thus easily digested and taken up. Whey is composed of several milk proteins one of which (glycomacropeptide (GMP) also known as Caseino Macro Peptide) induces one of the satiety hormones (CCK) in the stomach. In addition if included in a fibre tablet the solubility of the protein will facilitate the rapid dissolution of the fibre preparation in the stomach.

Preferred as a chemical satiety inducer is GMP or a GMP-containing concentrate and/or isolate.

The legume protein hydrolysate of the dietary supplement may be obtained from a plant of family Fabaceae and selected from the group of Alfalfa (*Medicago sativa*), clover (*Trifolium* species), peas (*Pisum sativum*), beans (*Phaseolus* species), lentils (*Lens culinaris*), lupins (*Lupinus* species), mesquite (*Prosopis* species), carob (*Ceratonia siliqua*), soy (*Glycine max*), and peanut (*Arachis hypogaea*).

Preferred is *Glycine max, Pisum sativum, Phaseolus vulgaris, Psophocarpus tetragonolobus*, and *Cicer arientimum*. The protein hydrolysate or proteinase inhibitor of the dietary supplement may also be obtained from a plant from the genus *Solanum* such as *Solanum tuberosum*.

In a preferred embodiment the fibre is dissolved in a hot liquid e.g. hot water either at the time of manufacture or shortly before ingestion. Preferred fibres are alginate, galacto- and glucomannans (xx-mannans) and pectin. More preferred fibres are alginate and xx-mannans. Most preferred is alginate.

The temperature suitable to dissolve the fibre in the liquid e.g. in water depends on the concentration of the fibre and the type of fibre. Preferably the temperature is at least 70° C., such as at least 80° C., e.g. at least 90° C. Also preferred is a temperature where the liquid is boiling e.g. 100° C.

The fibre of the dietary supplement can be used for two purposes. 1. only for absorbing/adsorbing liquid to fill out part of the stomach when ingested. 2. to encapsulate ingredients with a strong or unpleasant taste or effect in the mouth and also to absorbing/adsorbing liquid to fill out part of the stomach when ingested. Fibres for the two purposes can be prepared separately and combined when the dietary supplement is manufactured or the customer itself can combine the fibres before ingestion. Also the customer can ingest the fibres with the two mentioned purposes separately.

Proteinase Inhibitor

As described above proteinase inhibitors are chemical satiety inducers. Proteinase inhibitors are also known as protease inhibitors and peptidase inhibitors. Herein the term "proteinase inhibitor" is used to described molecules that inhibit the function of proteases i.e. inhibit enzymes that degrade proteins. Thus "protease inhibitors" and "peptidase inhibitors" are included when describing "proteinase inhibitor" herein.

A preferred chemical satiety inducer in the dietary supplement is at least one proteinase inhibitor. Many naturally occurring protease inhibitors are proteins. In a more preferred embodiment at least one proteinase inhibitor is present in the dietary supplement. Further preferred is when the at least one proteinase inhibitor is obtained from plants and/or algae.

Preferably the at least one proteinase inhibitor is obtained from a plant such as from potato and/or from a leguminous plant. Preferably the at least one proteinase inhibitor is obtained from a plant of a genus selected from the group of: potato (*Solanum*), pea (*Pisum*), bean (*Phaseolus*), broad bean (*Vicia*), chickpea (*Cicer*), soybean (*Glycine*).

The at lease one proteinase inhibitor can be obtained from a plant species selected from the group of: Alfalfa (*Medicago sativa*), clover (*Trifolium* species), peas (*Pisum sativum*), beans (*Phaseolus* species), broad bean (*Vicia faba*), lentils (*Lens culinaris*), lupins (*Lupinus* species), chickpea (*Cicer arietinum*), mesquite (*Prosopis* species), carob (*Ceratonia siliqua*), soy (*Glycine max*), and peanut (*Arachis hypogaea*) and potato (*Solanum tuberosum*).

Preferred is when the proteinase inhibitor is obtained from one or more of the plant species *Glycine max, Pisum sativum, Phaseolus vulgaris, Psophocarpus tetragonolobus, Cicer arientimum* and *Solanum tuberosum*.

The amount of the proteinase inhibitor in the dietary supplement is preferably about 0.01 to 20 mg per dose. More preferably it is 0.05 to 5 mg per dose. Further preferred is 0.1 to 2 mg proteinase inhibitor per dose.

In a preferred embodiment the dietary supplement comprises proteinase inhibitor and GMP. In a more preferred embodiment the dietary supplement comprises alginate, proteinase inhibitor and GMP.

Thermogen

A thermogen is preferably added to the dietary supplement to maintain and/or increase the metabolism of the individual.

The total amount of the at least one thermogen in the dietary supplement can be 0.5-15 mg/dose, such as 1-10 mg/dose, such as 1.5-5 mg/dose. When the thermogen is in the form of dry chilli powder made from chilli fruits, it has been found that a suitable dose is 0.5-5 g/L or 2.5-25 g/kg of a liquid and more dry product respectively.

In an embodiment the at least one thermogen of the dietary supplement is selected as plant parts or extracts of plant parts from the group of plants of *Camellia sinensis, Citrus aurantium, Helianthemum glomeratum, Zingiber officinale, Aframomum melegueta, Ephedra, Capsicum annuum, Capsicum frutescens, Physostigma venenosum, Hippomane mancinella, Anethum graveolens, Piper cubeba, Piper longum, Piper nigrum, Piper umbellatum, Habzelia aethiopica, Sinapis alba*, and/or *Armoracia rusticana*.

Hot spices such as chilli, mustard and horseradish have a thermogenic effect and the effect has been observed for the active ingredient in *Capsicum* i.e. for capsaicin. Furthermore, capsaicin has been demonstrated to down regulate appetite.

Chilli is a harmless thermogen that has shown no dangerous side effect and is regarded as a common foodstuff. The hot taste of chilli is perceived as unpleasant by some people, and therefore the taste may need to be masked. This may be trivial if the product is a pill but if the product is a powder or granulate the capsaicin (chillies active ingredient) may need to be encapsulated in the fibre product. The capsaicin may be bound directly to the fibre via hydrostatic interactions and thus avoid being perceived orally.

The diversity of chillies makes it possible to use one or more chilis in the dietary product described herein and make the product different in respect of the effect on the energy burning effect in an individual. Below the strength of different compounds and different chillies are compared to pure capsaicin:

| Scoville rating | Type of pepper |
| --- | --- |
| 15,000,000-16,000,000 | Pure capsaicin |
| 8,600,000-9,100,000 | Various capsaicinoids (e.g. homocapsaicin, homodihydrocapsaicin, nordihydrocapsaicin |
| 5,000,000-5,300,000 | Law Enforcement Grade pepper spray, FN 303 irritant ammunition |
| 855,000-1,050,000 | Naga Jolokia |
| 350,000-580,000 | Red Savina Habanero |
| 100,000-350,000 | Habanero chili, Scotch Bonnet Pepper, Datil pepper, Rocoto, Jamaican Hot Pepper, African Birdseye, Madame Jeanette |
| 50,000-100,000 | Thai Pepper, Malagueta Pepper, Chiltepin Pepper, Pequin Pepper |
| 30,000-50,000 | Cayenne Pepper, Aji pepper, Tabasco pepper, some Chipotle peppers |
| 10,000-23,000 | Serrano Pepper, some Chipotle peppers |
| 2,500-8,000 | Jalapeño Pepper, Guajillo pepper, New Mexican varieties of Anaheim pepper, Paprika (hungarian wax pepper) |
| 500-2,500 | Anaheim pepper, Poblano Pepper, Rocotillo Pepper |
| 100-500 | Pimento, Pepperoncini |

The Scoville rating is proportional to the concentration of the active compound when the active compound is capsicin.

The thermogen of the dietary supplement may also be at least one compound from the vanilloid family and/or at least one compound known to be a vanilloid receptor agonist. These compounds may be combined with other thermogens in the dietary supplement.

By a "vanilloid" is meant a compound comprising a vanniloid moity such as vanillin (4-hydroxy-3-methoxybenzaldehyde) with different side groups. Vanilloids include e.g. vanillin, vanillic acid, capsaicin and vanillyl mandelic acid (VMA).

By vanilloid agonist is meant a compound having the same effect on the vanilloid receptors as vanilloids.

The compound from the vanilloid receptor agonist family may be selected from the group of capsaicin, capsainoid, piperin, gingerol, zingiberin, vanillin and/or vanillic acid and/or derivates hereof.

The at least one thermogen may also be other compounds that function as an agonist of the vanilloid receptor or being functional vanilloid analogs. Such compounds may be an unsaturated sesquiperpene dialdehyde such as warburganal from *Warburgia ugandensis* and/or *W. stuhlmannii*, which functions as an agonist upon the V-receptors. Other examples of agonists are polygodial from *Polygonum hydropiper* (waterpepper). Also the sesquiterpenes cinnamolide, cinnamodial, cinnamosmolide (from *Cinnamosmo fragrans*) and/or isovalleral from *Lactarius vellerius* (a fungus) can be used as thermogens. Also triprenyl phenols may be used as thermogens, e.g. Scutigeral from *Albatrellus ovinus*, (a fungus).

The chemical satiety inducer and the thermogen may be obtained from plant parts from plants belonging to the group of *Capsicum annuum, Capsicum frutescens, Capsicum chinense, Capsicum pubescens*, and/or *Capsicum baccatum*. Preferred are plant parts from *Capsicum annuum* and *Capsicum frutescens*. The compounds capsaicin and/or capsainoids are also preferred for the dietary supplement. The intake of dietary supplement corresponding to about 1 mg of capsaicin and/or capsainoids 3 to 6 times a day may be sufficient for reducing or keeping the weight of an individual.

The chemical satiety inducer and/or the thermogen may be a compound selected from the group of capsaicins, capsaicinoids, piperins, zingiberins, gingerols, vanillin and/or vanillic acid and/or allylisothiocyanat and/or glycosides of these compounds.

The capsaicinoids to be used in the dietary supplement may be selected from the group of homocapsaicin, homodihydrocapsaicin, nordihydrocapsaicin, capsaicin, dihydrocapsaicin, norcapsaicine, and/or zucapsaicin.

Side Effect Remover

In order to reduce and/or eliminate flatulence and relieve abdominal pain induced by ingestion of large amounts of fibre, herbal plant parts and/or a herbal extract with the function as a side effect remover can be included in the dietary product. One possible choice of a side effect remover could be plant parts from a species of the genus *Mentha* in any form but also a number of other herbs may have a similar effect. These herbs are described herein.

The amount of the at least one side effect remover of the dietary supplement may corresponds to the amount of the at least one side effect remover in 10-1000 µl oil per dose when an extract of plant material containing the at least one side effect remover is prepared, such as 20-900 µl, such as 30-800 µl, such as 40-700 µl, such as 50-600 µl, such as 60-500 µl, such as 70-400 µl, such as 80-300 µl, such as 90-200 µl, such as 100-150 µl.

The dietary supplement may include a side effect remover which can be obtained as plant parts or extract obtained from one or more plants of the group of *Levisticum officinale* (Lovage), *Mentha* spp, *Mentha spicata* (Spearmint), *Piper nigrum* (Pepper) Fruit, *Thymus vulgaris* (Thyme), *Anethum graveolens* (Dill), *Camellia sinensis* (Tea), *Glycyrrhiza glabra* (Licorice), *Ocimum basilicum* (Basil), *Rosmarinus officinalis* (Rosemary), *Ocimum gratissimum* (Agbo), *Mentha pulegium* (European Pennyroyal), *Myrtus communis* (Myrtle), *Sassafras albidum* (Sassafras), *Satureja montana* (Savory), *Thymus capitatus* (Spanish Thyme), *Zea mays* (Corn), *Acinos suaveolens, Micromeria congesta* (Kaya Yarpuzu), *Origanum minutiflorum* (Small-Flowered Oregano), *Origanum vulgare* (Oregano), and/or *Acorus calamus* (Calamus)

The plants of the *Mentha* may be any of the following *Mentha* species: *Mentha aquatica, Mentha arvensis, Mentha asiatica, Mentha australis, Mentha canadensis, Mentha cervina, Mentha citrate, Mentha crispate, Mentha cunninghamia, Mentha dahurica, Mentha diemenica, Mentha gattefossei, Mentha grandiflora, Mentha haplocalyx, Mentha japonica, Mentha kopetdaghensis, Mentha laxiflora, Mentha longifolia, Mentha sylvestris, Mentha pulegium, Mentha requienii, Mentha sachalinensis, Mentha satureioides, Mentha spicata, Mentha cordifolia, Mentha suaveolens, Mentha vagans, Mentha×gracilis, Mentha×piperita, Mentha×rotundifolia (M. longifolia×M. suaveolens), Mentha×smithiana (M. aquatica×M. arvensis×M. spicata), Mentha×villosa (M. spicata×M. suaveolens), Mentha nemorosa,* and/or *Mentha× villosonervata*. Preferred plant parts are e.g. extract of *Mentha spicata* (Spearmint) and *Mentha×piperita*.

The side effect remover can also be selected from the group of *Foeniculum vulgare, Pimpinella anisum, Melissa officinalis, Taraxacum officinale, Aloe vera, Iberis amara, Chamomilla recutita, Citrus aurantium, Cnicus benedictus, Elettaria* spp., *Amomum* spp., *Centaurium erythracea, Cichorium intybus, Cinnamomum verum, Coriandrum sativum, Gentiana* spp., *Juniperus, Tilia* spp., *Raphanus sativus, Rosmarinus officinalis, Salvia officinalis, Hypericum perforatum,* and *Peumus boldus.*

The side effect remover can also be selected from the group of mint oils, menthol, menthone, methyl ester, thymol, cymene and/or citronellal. By "mint oil" is meant an extract based on fresh or dried plant material of a plant species of the genus *Mentha*. All the plants of the genus *Mentha* are believed to contain at least about five of the six compounds menthol, menthone, methyl ester, thymol, cymene and citronellal. Any *Mentha* species containing at least five of these compounds is a preferred side effect remover for the dietary supplement as described herein.

A thermogen and/or side effect remover may for some people have an unpleasant taste and it can therefore be a benefit to encapsulate these compounds. Encapsulation of thermogen also have the benefit that a possible "burning effect" need not be present in the mouth of an individual if the thermogen is encapsulated and released in the stomach and/or intestine.

In an embodiment the dietary supplement comprises at least one chemical satiety inducer and/or at least one thermogen and/or at least one side effect remover which can be encapsulated. Alternatively at least one chemical satiety inducer and at least one thermogen may be encapsulated. Or at least one chemical satiety inducer and at least one side effect inducer may be encapsulated. Also at least one thermogen and at least one side effect inducer may be encapsulated.

Preferably at least one thermogen of the dietary supplement is encapsulated. More preferred, at least one side effect inducer is encapsulated. Even more preferred is when at least one thermogen and at least one side effect inducer are encapsulated.

In the dietary supplement at least one chemical satiety inducer and/or at least one thermogen and/or at least one side effect remover may be encapsulated in a fibre. Any fibre mentioned herein may be used for the encapsulation. The encapsulation may be performed by entrapment in a gel of a fibre and/or by hydrostatic binding to one or more fibre type. Encapsulation of at least one thermogen and/or at least one side effect remover may also be performed by hydroxypropyl cellulose.

Preferably, the fibre used for encapsulation is alginate, hydroxypropyl methyl cellulose, pectin, clucomannan, cellulose, and/or chitosan. The compounds to be encapsulated may be encapsulated into a small portion of the fibre used for the dietary supplement or the compounds may be encapsulated in standard gelatine capsules. The fibre used for encapsulation may be 0.05-5% of the total amount of the fibre in the dietary supplement. Preferably, the fibre used for encapsulation is 0.1-3% of the total amount of the fibre in the dietary supplement, more preferably 0.15-2%, most preferably 0.2-1%.

Combinations of the Compounds

The dietary supplement may contain any fibre mentioned herein combined with any chemical satiety inducer mentioned herein combined with any thermogen mentioned herein combined with any side effect remover mentioned herein.

When producing the dietary supplement it is possible to use plant material from less than three plant species or to use a whey product combined with plant material from one species, and still obtain the function of a chemical satiety inducer, a thermogen, and a side effect remover within the dietary supplement. To obtain this effect only two different compounds or plant parts from two plants, or one compound together with plant parts from one plant are used in the dietary supplement to fulfil these three requirements. Also a whey product combined with plant parts from a single plant may fulfil the three requirements e.g. whey combined with plant parts from chilli (*Capsicum*) (effective compound e.g. capsaicin). One ingredient e.g. parts from a single plant may have the effect of function as a chemical satiety inducer and as a thermogen; as a chemical satiety inducer and as a side effect remover; as a thermogen and a side effect remover; or as a chemical satiety inducer, a thermogen and a side effect remover. The following plants can be used both as a thermogen and as a side effect remover, thus plant parts e.g. extracts from at least one of these plants can fulfil the requirement of both a thermogen and a side effect remover: *Anethum graveolens, Camellia sinensis* (Tea), *Piper nigrum* (Pepper), *Zingiber officinale, Capsicum annuum, Capsicum frutescens*.

The plants *Anethum graveolens, Piper nigrum* (Pepper), *Zingiber officinale, Capsicum annuum, Capsicum frutescens* all comprises compounds of vanilloids or vanniloid agonists as described elsewhere herein. These plants also comprise 3-6 carminative compounds selected from the group of anethole, camphor, carvacrol, carvone, copaene, ethyl-acetate, eugenol, menthol, methyl salicylate, piperine, safrole, thymol, thymyl-acetate, gingerol, and capsaicin. These compounds or plant parts comprising these compounds can be used in the dietary supplement.

*Camellia sinensis* comprises the thermogenic compound Epigallocatechin gallate.

A dietary supplement may be produced, wherein only one compound together with plant parts from one plant can be used to fulfil the three requirements of chemical satiety inducer, thermogen, and side effect remover. This may be obtained by combining a protein hydrolysate such as whey, soy bean hydrolysate, proteinase inhibitor from potato (*Solanum tuberosum*) and/or pea hydrolysate with plant parts of *Anethum graveolens, Camellia sinensis* (Tea), *Piper nigrum* (Pepper), *Zingiber officinale, Capsicum annuum, Capsicum frutescens*. Preferred as a protein hydrolysate is pea hydrolysate. More preferred is soy bean hydrolysate. Most preferred is whey.

Another possibility to fulfil the three requirements mentioned above can be obtained by combining any of the compounds selected from the group of whey, soy bean hydrolysate and/or pea hydrolysate with any of the compounds selected from the group of capsaicin, capsaicinoids, piperin, gingerol, and zingiberin.

Furthermore two compounds having the three effects as described above may be obtained by combining GMP from whey or a Kunitz type protease Inhibitor or a bowman-birk type protease Inhibitor obtained from legume or a PI2 (potato proteinase inhibitor II) type protease inhibitor from potato with plant parts from any of the plants selected from the group of *Anethum graveolens, Camellia sinensis, Piper nigrum, Zingiber officinale, Capsicum annuum, Capsicum frutescens*.

Yet another possibility to fulfil the three requirements mentioned above can be obtained by combining GMP from whey or a Kunitz type protease inhibitor or a bowman-birk type protease Inhibitor obtained from a legume or a PI2 type protease inhibitor from potato with any of the compounds selected from the group of Capsaicin, Capsaicinoids, piperin, gingerol, and zingiberin.

In a preferred embodiment at least three different compounds and/or plant parts e.g. extract from at least three different plants are used in the dietary supplement to fulfil the requirements of a chemical satiety inducer, a thermogen, and a side effect remover.

The chemical satiety inducer may be obtained from any plant described herein as a chemical satiety inducer, the thermogen may be obtained from any plant described herein as a thermogen, and the side effect remover may be obtained from any plant described herein as a side effect remover. Any combination of plants of the three groups are possible.

In an embodiment the chemical satiety inducer can be GMP from whey or a Kunitz type protease inhibitor and/or a bowman-birk type protease inhibitor obtained from legume or the chemical satiety inducer can be any of the compounds capsaicin, capsaicinoids, piperin, gingerol, or zingiberin. These chemical satiety inducers may be combined with parts of plants comprising a thermogen, the plants can be selected from a the group of *Camellia sinensis, Helianthemum glomeratum, Zingiber officinale, Aframomum melegueta, Ephedra, Capsicum annuum, Capsicum frutescens, Physostigma venenosum, Hippomane mancinella, Anethum graveolens, Piper cubeba, Piper longum, Piper nigrum, Piper umbellatum, Habzelia aethiopica, Sinapis alba*, and/or *Armoracia rusticana* or the thermogen can be selected from the group of compounds of (+)-pseudoephedrine, (−)-ephedrine, (−)-epigallocatechin-gallate, (−)-pseudoephedrine, 10-gingerol, 6-gingerol, 6-shogaol, 8-gingerol, 8-shogaol, capsaicin, cathinone, conjugated-linoleic-acid, isothiocyanate, physostigmine. The combinations of chemical satiety inducers and thermogens just mentioned may be combined with plant parts having effect as a side effect remover, these plants being selected from the group of plants of *Levisticum officinale, Mentha, Mentha spicata, Piper nigrum, Thymus vulgaris, Anethum graveolens, Camellia sinensis, Glycyrrhiza glabra, Ocimum basilicum, Rosmarinus officinalis, Ocimum gratissimum, Mentha pulegium, Myrtus communis, Sassafras albidum, Satureja montana, Thymus capitatus, Zea mays, Acinos suaveolens, Micromeria congesta, Origanum minutiflorum, Origanum vulgare, Acorus calamus, Foeniculum vulgare, Pimpinella anisum, Melissa officinalis, Taraxacum officinale, Aloe vera, Iberis amara, Chamomilla recutita, Citrus aurantium, Cnicus benedictus, Elettaria* spp., *Amomum* spp., *Centaurium erythracea, Cichorium intybus, Cinnamomum verum, Coriandrum sativum, Gentiana* spp., *Juniperus, Tilia* spp., *Raphanus sativus, Rosmarinus officinalis, Salvia officinalis, Hypericum perforatum*, and/or *Peumus boldus*. Any *Mentha* mentioned herein can be used as a side effect remover. Also the side effect remover can be selected from the group of compounds of anethole, camphor, carvacrol, carvone, copaene, ethyl-acetate, eugenol, menthol, methyl salicylate, piperine, safrole, thymol, thymyl-acetate, gingerol, and capsaicin.

In an embodiment, the dietary supplement comprises a fibre, a chemical satiety inducer, a thermogen and a side effect remover. The dietary supplement may comprise a combination of at least one fibre selected from the group of galactomannan, glucomannan, pectin, arabinoxylan, cellulose, alginate, and chitosan. This fibre may be combined with at least one chemical satiety inducer selected from the group of GMP from whey, a Kunitz type or a Bowman-Birk type protease inhibitor obtained from legume, capsaicin, capsaicinoids, piperin, gingerol, or zingiberin. A combination of fibre and chemical satiety inducer may be combined with parts of plants comprising a thermogen, the plants can be selected from a the group of *Camellia sinensis, Helianthemum glomeratum, Zingiber officinale, Aframomum melegueta, Ephedra, Capsicum annuum, Capsicum frutescens, Physostigma venenosum, Hippomane mancinella, Anethum graveolens, Piper cubeba, Piper longum, Piper nigrum, Piper umbellatum, Habzelia aethiopica, Sinapis alba*, and/or *Armoracia rusticana* or the thermogen can be selected from the group of compounds of (+)-pseudoephedrine, (−)-ephedrine, (−)-epigallocatechin-gallate, (−)-pseudoephedrine, 10-gingerol, 6-gingerol, 6-shogaol, 8-gingerol, 8-shogaol, capsaicin, cathinone, conjugated-linoleic-acid, isothiocyanate, and physostigmine. The combinations of fibre, chemical satiety inducers and thermogens just mentioned may be combined with plant parts having effect as a side effect remover, these plants may be selected from the group of plants of *Levisticum officinale*, *Mentha*, *Mentha spicata*, *Piper nigrum*, *Thymus vulgaris*, *Anethum graveolens*, *Camellia sinensis*, *Glycyrrhiza glabra*, *Ocimum basilicum*, *Rosmarinus officinalis*, *Ocimum gratissimum*, *Mentha pulegium*, *Myrtus communis*, *Sassafras albidum*, *Satureja montana*, *Thymus capitatus*, *Zea mays*, *Acinos suaveolens*, *Micromeria congesta*, *Origanum minutiflorum*, *Origanum vulgare*, and/or *Acorus calamus*. Any *Mentha* mentioned herein can be used as a side effect remover. Also the side effect remover can be selected from the group of compounds of anethole, camphor, carvacrol, carvone, copaene, ethyl-acetate, eugenol, menthol, methyl salicylate, piperine, safrole, thymol, thymyl-acetate, gingerol, and capsaicin.

Preferred combinations of chemical satiety inducers, thermogens and side effect removers are listed in the table below.

| Chemical satiety inducer | Thermogen | Side effect remover |
|---|---|---|
| Whey protein and/or GMP | *Capsicum frutescens* (capsaicin) | *Mentha piperita* *Thymus vulgaris* *Glycyrrhiza glabra* *Ocimum basilicum* *Origanum vulgare* |
| | *Capsicum annuum* (capsiate, dihydrocapsiate, nordihydrocapsiate) | *Mentha piperita* *Thymus vulgaris* *Glycyrrhiza glabra* *Ocimum basilicum* *Origanum vulgare* |
| | *Zingiber officinale* (zingiberol) | *Mentha piperita* *Thymus vulgaris* *Glycyrrhiza glabra* *Ocimum basilicum* *Origanum vulgare* |
| | *Piper niger* (piperin) | *Mentha piperita* *Thymus vulgaris* *Glycyrrhiza glabra* *Ocimum basilicum* *Origanum vulgare* |
| | *Albatrellus ovinus* (scutigeral) | *Mentha piperita* *Thymus vulgaris* *Glycyrrhiza glabra* *Ocimum basilicum* *Origanum vulgare* |
| Soy protein hydrolysate and/or soybean proteinase inhibitor | *Capsicum frutescens* (capsaicin) | *Mentha piperita* *Thymus vulgaris* *Glycyrrhiza glabra* *Ocimum basilicum* *Origanum vulgare* |
| | *Capsicum annuum* (capsiate, dihydrocapsiate, nordihydrocapsiate) | *Mentha piperita* *Thymus vulgaris* *Glycyrrhiza glabra* *Ocimum basilicum* *Origanum vulgare* |
| | *Zingiber officinale* (zingiberol) | *Mentha piperita* *Thymus vulgaris* *Glycyrrhiza glabra* *Ocimum basilicum* *Origanum vulgare* |
| | *Piper niger* (piperin) | *Mentha piperita* *Thymus vulgaris* *Glycyrrhiza glabra* *Ocimum basilicum* *Origanum vulgare* |
| | *Albatrellus ovinus* (scutigeral) | *Mentha piperita* *Thymus vulgaris* *Glycyrrhiza glabra* *Ocimum basilicum* *Origanum vulgare* |
| Pea protein hydrolysate and/or pea proteinase inhibitor | *Capsicum frutescens* (capsaicin) | *Mentha piperita* *Thymus vulgaris* *Glycyrrhiza glabra* *Ocimum basilicum* *Origanum vulgare* |
| | *Capsicum annuum* (capsiate, dihydrocapsiate, nordihydrocapsiate) | *Mentha piperita* *Thymus vulgaris* *Glycyrrhiza glabra* *Ocimum basilicum* *Origanum vulgare* |
| | *Zingiber officinale* (zingiberol) | *Mentha piperita* *Thymus vulgaris* *Glycyrrhiza glabra* *Ocimum basilicum* *Origanum vulgare* |
| | *Piper niger* (piperin) | *Mentha piperita* *Thymus vulgaris* *Glycyrrhiza glabra* *Ocimum basilicum* *Origanum vulgare* |
| | *Albatrellus ovinus* (scutigeral) | *Mentha piperita* *Thymus vulgaris* *Glycyrrhiza glabra* *Ocimum basilicum* *Origanum vulgare* |

The combinations mentioned in the table may be combined with any fibre. Preferred is when the above mentioned combinations are combined with a fibre of alginate, galactomannans, glucomannans and/or pectin. These fibres may form gels, which is a preferred characteristic of the fibre.

Also each of the combinations mentioned in the table may be combined with potato proteinase inhibitor. Each of the combination comprising potato proteinase inhibitor may further be combined with a fibre, preferably fibre of alginate, galactomannans, glucomannans and/or pectin.

Products

The dietary supplement as described herein may be in the form of powder, pills, tablets, capsules, gel, and/or liquid. The dietary supplement may be in a non-liquid form when the consumer buys it, however, it may also be an integrated part of a solid or liquid foodstuff.

The dietary supplement may be a product which is ready-to-eat. The dietary supplement may also be a product which is ready-to-drink. However, the dietary supplement may also be a product which should be added to a liquid just before ingestion. With "just before ingestion" is meant that the dietary product supplemented with a liquid is preferably ingested by an individual within 30 minutes from bringing the dietary product into contact with the liquid, such as within 20 min, e.g. within 15 min, such as within 10 min, e.g. within 5 min, e.g. within 2 min. The dietary supplement may be a powder which is mixed with cold water and ingested (e.g. by drinking) immediately after mixing the powder and the water, the mixture may be stirred before ingestion.

The dietary product may be part of a foodstuff which is intended to heat with or without adding further ingredients. E.g. the dietary product may be part of a soup, which is cooked before ingested by an individual.

When the dietary supplement is a beverage the liquid e.g. water of the beverage may be above 80%, such as above 85%, such as above 87%, such as above 90%, such as above 92%, such as above 95%, such as above 97%. Preferably the liquid content is 90-99%, such as 90-99% of water.

The gel strength of the dietary supplement is preferably below 10 KPa, such as below 9 KPa, such as below 8 KPa, such as below 7 KPa, such as below 6 KPa, such as below 5 KPa, such as below 4 Kpa, such as below 3 KPa. Preferably the gel strength is between 1 and 5 KPa, more preferably between 2 and 4 KPa. The strength of the dietary supplement is determined in respect to the product after a gel has formed i.e. when the dietary supplement is in the form of ready to ingest and is contacted with gastric acid or calcium or an acid is added which induce the formation of a gel. The strength is described in Draget et al (Alginic acid gels: the effect of alginate chemical composition and molecular weight. Carbohydrate Polymers 1994: 25, 31-38).

The dietary supplement as described herein may be produced in doses, where one dose or one unit dose of the dietary supplement comprises:
   An amount of at least one mechanical satiety regulator corresponding to 0.5-3 gram in total of fibre,
   An amount of at least one chemical satiety inducer corresponding to 10-100 mg in total of milk protein and/or of legume protein hydrolysate and/or of potato protein hydrolysate,
   An amount of at least one thermogen comprising compounds corresponding to 1.5-4 mg in total of compounds of the vanilloid family and/or 1.5-4 mg of a vanilloid receptor agonist, and
   An amount of at least one side effect remover corresponding to 150-250 microliter of mint oil.

A preferred amount in the unit dose of compounds of the vanilloid family is 2 mg. A preferred amount in the unit dose of mint oil is 200 microliter.

Minerals and vitamins can also be included in the dietary product. Especially minerals and vitamins in amounts recommended by the authority are suitable.

The dietary supplement may be included in a food product such as a ready-made meal. The food product into which the dietary supplement can be included may be ready-made meals, biscuits, crispbread, chips, snack bars, beverages, cookies, yoghurt, ice cream, noodles, pudding, jellies, sauces, salsas and toppings.

The dietary supplement as described herein may be included in a food product and the dietary supplement may constitute 0.5-10% (w/w or w/v) of the product.

For liquid products (soups, sauces, icecream, yoghurt, salsas, milk, beverages) is it preferred when the dietary supplement constitutes about 0.25-1.5 (w/v) of the product. Expressed as the amount of the individual active constituents, a liquid product typically contains around 0.25-2.5 g/L of mechanical satiety regulator such as alginate, 10-250 mg/L of a chemical satiety regulator such as whey protein, 0.5-2.5 ml/L of a side-effect remover such as mint oil, or an equivalent amount of mint leaves, and 0.5-5 g/L of a thermogen such as dry chillipowder or an equivalent amount of fresh chilli fruits.

For more dry food products such as bakery, cookies, chips etc it is preferred when the dietary supplement constitutes 2-5% (w/w) of the food product. Expressed as the amount of the individual active constituents, a product of this type typically contains around 0.5-10 g/kg of mechanical satiety regulator such as alginate, 25-500 mg/kg of chemical satiety regulator such as whey protein, 0.5-10 ml/kg of a side-effect remover such as mint oil, or an equivalent amount of mint leaves, and 2.5-25 g/kg of a thermogen such as dry chillipowder or an equivalent amount of fresh chilli fruits.

The dietary supplement as described herein need not be incorporated in a food product, and can be a product which is ingested shortly before ingestion of a meal or is ingested instead of a meal. In that case, the dietary product typically constitutes 80-100% of the product, which may be powder, pills, or capsules. This amount refers to the total amount of mechanical satiety inducing regulator, as well as any optional divalent cation and compound capable of complexing calcium, chemical satiety inducer, optional thermogen and optional side-effect remover.

Production and Use of the Dietary Supplement

An aspect of the invention relates to a method for the production of a dietary supplement as described elsewhere herein, wherein the ingredients are mixed into one or more products which are to be ingested by an individual.

In a preferred embodiment the dietary supplement is a two-component product. The one product, a fibre product, comprises alginate and whey protein, the other product comprises chilli (*Capsicum* species) and mint (*Mentha* species). The fibre product can be produced by heating a suspension of alginate in water (0.125-1%) to a temperature of 70-100° C. and shaking and stirring the heated suspension. The solution is cooled. When the solution has a temperature of 20-30° C. whey or whey protein is added with an amount corresponding to 1-100 mg of whey protein per 100 ml of liquid. The fibre product is then ready to ingest and may be bottled for sale or incorporated into another drink. Extracts of chilli (*Capsicum* species) and mint (*Mentha* species) can be encapsulated into beads of alginate gel. A solution of alginate is prepared by heating a suspension of Na-alginate in water to 70-100° C. Extracts of chilli and mint is added when the temperature of the solution is below 70° C. The beads are formed by dripping drops of the solution into a Ca-containing solution or into acid. When formed, the beads may be used directly or they may be freeze dried and stored before use. The beads are ready to ingest and may be integrated into a drink or may be manufactured separately to be ingested simultaneous with the fibre drink or shortly before or shortly after ingestion of the fibre drink. Instead of alginate beads, the extracts of chilli and mint may be encapsulated into capsules which can be ingested together with the fibre drink.

The alginate beads can be used in a dietary product as non-dried beads or as dried beads. The treatment of the beads in this respect depends on the formulation of the dietary product. When used in a fibre drink the alginate beads need not be dried. When used in a dry composition e.g. a powder or a dry composition for a soup etc, the alginate beads can be dried before mixed with other dry ingredients e.g. dried vegetables. The dried vegetables may include plant parts of *Capsicum* species and/or of *Mentha* species.

In a specific aspect when the fibre is alginate is a method for the production of a dietary product, wherein the alginate fibre is heated to above 70° C. Preferably the alginate fibre is mixed into a liquid before performing the heating. The alginate fibre may be heated before incorporated into a dietary product i.e. before sale. Alternatively the alginate fibre may be incorporated into a dietary product which is distributed without a heating of the alginate fibre, and this product should preferably be heated before ingested by an individual. As indicated the fibre should preferably be heated to a temperature above 70° C., e.g. above 75° C., such as above 80° C., e.g. above 85° C., such as above 90° C., e.g. above 95° C., even boiling can be used.

An aspect of the invention relates to use of the dietary supplement described herein or of a food product described herein to obtain a reduced weight of an individual and/or to prevent weight increase of an individual.

The individual to ingest the dietary supplement and/or food product can be any human or animal. Preferred is the group of humans, dogs, cats, horses. More preferred the individual is a human. The dietary supplement and food products can be used both for male and female, as well as for children and adults.

Preferably an individual when using the dietary supplement ingests an amount of dietary supplement comprising 3-25 gram of fibre per day. The daily intake of the dietary supplement as described herein may be determined in respect to how much an individual would reduce caloric intake. If e.g an individuals stomach can contain about 600 ml of food, a reduction of the volume by about 50% correspond to an intake of the dietary supplement equivalent to 300 ml gel for each meal.

Preferred is a use of the dietary supplement where the individual ingests an amount of the product corresponding to about 0.3-3 gram of fibre 3-5 times a day. A use where an individual ingests about 0.5-2 gram of the product 3-5 times a day is also possible.

The use of the dietary product may also be where an individual when being awake ingests at least 0.3 g of the product with intervals of at least 2 hours.

A preferred use of the dietary supplement is when ingested by an individual within 60 minutes before the individual is having a meal. More preferred is ingestion of the dietary supplement 5-30 minutes before having a meal.

The use of the dietary supplement may be when the dietary supplement constitutes 10-80% of the volume of a meal such as 25-75%. Preferred is a use of the product where the dietary supplement constitutes about 50% of a meal. Some observation of meal size indicates the weight of a lunch to be between 480 and 680 g giving an average of app. 500 g. Considering that the average person drinks 0.25 litre of fluid with the meal, the average volume of a lunch would be 750 ml. Measurement of gastric volumes using either baroscopy or tomography shoved an average fasting volume (73 persons) of 213 ml while after eating the volume was 698 ml. The full male stomach volume is in general slightly larger than the female stomach. Therefore aiming at a given (speed of) weight loss the product as described herein could take up 300 to 600 ml of gastric volume for each meal. If the volume of the stomach is about 700 ml, a dietary supplement of 300 to 600 ml corresponds to 40-80% of the volume of the stomach.

An aspect of the invention relates to a kit of parts comprising at least two foodstuffs which are to be ingested together or shortly after each other. The at least two foodstuffs when taken together is a dietary supplement as described elsewhere herein.

The kit may be constructed such that one foodstuff is a dry or solid foodstuff and one foodstuff is a soft or liquid foodstuff.

The kit may also be assembled to include at least two foodstuffs which may be a combination of a biscuit-like foodstuff and a liquid foodstuff or a biscuit-like foodstuff and a creamy foodstuff. Such kits can be used as "between meals" snack for overweight children or adults. Biscuits/chips comprising fibre combined with a flavoured drink comprising whey e.g. as chips and chocolate milk, and where the chemical satiety inducer and the thermogen may be in the biscuits/chips and the side effect remover can be in the liquid drink. The kit may also be like the "Cheese dipper" principle with a biscuit and a cream/cheese to be ingested by dipping the biscuit into the cream/cheese.

All ingredients can be individually included in a kit and served e.g. as a drink with whey or whey and fibre, a flavour comprising a thermogen and/or a side effect remover e.g. mint, sweets comprising a thermogen and/or a side effect remover e.g. mint, a dip comprising fibre and comprising a thermogen and/or a side effect remover e.g. mint, chilli, balm, lavender, fennel and/or lovage, and chips/biscuits comprising fibre, a chemical satiety inducer e.g. whey and a thermogen and/or a side effect remover e.g. chilli.

When the dietary product is formed into pills, these can include all the ingredients of fibre, chemical satiety inducer, thermogen and side effect remover i.e. the product can be formed as an "All in one" product. These pills/capsules can be ingested by an individual by following a schedule indicating the time of intake or they can be ingested by the individual when being hungry.

The dietary product can also be a two component system. Such systems or kits ("A" plus "B") may be A) Fibre together with antiflatulence i.e. side effect remover combined with B) appetite regulators as a mixture of chemical satiety inducer and thermogens or A) Fibre together with appetite regulator (chemical satiety inducer and/or thermogens) combined with B) appetite regulator (chemical satiety inducer and/or thermogens) together with an antiflatulence (side effect remover)

or

A) Fibre combined with B) appetite regulators (thermogen) and antiflatulence (side effect remover) combined with whey drink Each of the components "A" and "B" in a two component system may be provided as a drink or pills/capsule. Bulky ingredients i.e. fibre may most conveniently be supplied as a drink while strong tasting ingredients may most conveniently be supplied in the form of pills/capsules Some simple systems include Plain, i.e. the consumer obtains the dietary product as a powder or granulate The consumer can obtain the product in larger containers/bags. The powder or granulate of the dietary product can be measured with teaspoon, or a specially designed measuring spoon before being ingested as part of a meal or dissolved in a liquid.

The consumer can obtain the product in portioned bags/containers and ingested as part of a meal or dissolved in a liquid.

The dietary product can be incorporated into biscuits or low energy bars

Biscuits or low energy bars can be used by an individual as a remedy against "between meals hunger"

The dietary product can be a convenience package.

concept being a package that provides everything except meat for a meal. Such a program could be adoptable for fish dishes, meat dishes, vegetarian dishes. The content of the ingredients, both food and dietary remedy, is calculated to give "normal" satiety with a desired low amount of calories. Suitable food stuffs for such a concept would be either frozen or dried or freeze dried.

Convenience packages could be sold in packages covering one day, one week or one month of use, and may be constructed to contain starters, main course and desserts.

If only the dietary supplement is sold the concept could be expanded by
  Providing different recipes and selling the product as an "add-on" to fresh food
The dietary product can be incorporated into disposable "shakers" with portioned powder or granulate or concentrated solutions
  The dietary product can be supplied with water, shaken and drunk. The volume of the shaker can indicate the amount of water needed. The shaker concept can be used by the consumer in a scheduled manner or be ingested due to the "when hungry" principle.
The dietary product can be provided as portions in a concentrated dissolved form in ampoules or squeeze tubes alongside with shakers
  The concentrate is then added to an amount of water defined by the volume of the shaker
The dietary remedy can be provided as a "snack pack"
  Biscuits and a flavoured drink
    Whey or whey/fibre drink combined with snack containing thermogen and anti flatulent
    Whey drink combined with biscuit containing fibre, thermogen and anti flatulant
    Fibre drink combined with biscuit containing whey, thermogen and anti flatulent.

Further Characteristics of the Dietary Supplement

The dietary supplement as described herein is in a preferred embodiment not formulated as a chewing gum. The intention of the present invention is to ingest the dietary supplement to make the fibre function in the stomach, where also the chemical satiety inducer can be released from the product and directly or indirectly affect the receptors for satiety signalling.

In another preferred embodiment the dietary supplement does not comprise enzymes obtained from bacteria. These enzymes, which can be absent from the dietary supplement can be protease and/or lipase, especially protease from *Aspergillus* and/or from *Bacillus* and lipase from *Aspergillus* can be absent from the dietary supplement.

The dietary supplement as described herein can be produced without the thermogens or metabolic speeders such as caffeine. Also epinephrine (ephedrine) can be avoided in the dietary product. Furthermore guarana may be a compound not used for the dietary supplement.

The dietary supplement as described herein is not intended for meal replacement. The intension of the present invention is to limit the amount of food ingested during normal meals while still obtaining satiety.

The dietary supplement as described herein is not necessarily intended to increase the daily consumption of fibre to conform with recommendations. The fibre is intended to gel in the gastric lumen in order to induce mechanical satiety signalling, and preferably the amount of fibre is the minimal amount necessary to form the needed volume of gel.

Form/Design of the Product

The fibre may be considered to define the design of the dietary supplement. Depending on gelling properties and rehydration properties of the fibre, the following 5 principal types of product, freeze dried gel, redissolved gel, solubilised fibre, gelled fibres and dry fibres, may be produced, each of which can be formulated in different ways, where some examples are outlined below.

1. Freeze dried gel. A freeze dried gel may include all ingredients such as chemical satiety inducer, thermogen and side effect remover. Freeze dried gels may be Ca-gels or acid gels.

Ca-gels may be of the types Alginate gels or pectin. The freeze dried gel may be used for the production of pills/capsules or dietary ingredients such as convenience food, biscuits, crispbread and noodles.

Acid gels may be prepared from alginate and may be used as pills or included in capsules.

2. Redissolved gel. A redissolved gel may be a Ca-induced gel titrated with e.g. citric acid. The redissolved product is freeze dried and may include all the ingredients of chemical satiety inducer, thermogen and side effect remover. The redissolved gel may be of the types Ca-gels of Alginate or pectin. The redissolved gel may be used to produce pills or dietary ingredients for convenience food, e.g. biscuits, crispbread and noodles.

3. Solubilised fibre. Solubilised fibre may be of the types, alginate, pectin or xx-mannans. These fibres may be used raw in drinks in a plain format or where the "strong" taste is encapsulated e.g. encapsulated in a part of the fibre used. The fibre used to encapsulate the plant parts with a strong taste or strong effect in the mouth, may be included in the other fibre part of the dietary product without encapsulated compounds, or the fibre with encapsulated compounds can be added to e.g. a drink as a soluble capsule or swallowed with a capsule. The solubilised fibre may also be used for a fibre drink or pill with the remaining ingredients.

4. Gelled fibres containing all ingredients. The Gelled fibre may be of alginate. It may be consumed/ingested in the form of puddings/jellies or layered biscuits.

5. Dry fibres. Dry fibres may be of any of the fibre mentioned herein. The use may be plain i.e. as an ingredient in hot meals or hot drinks.

DETAILED DESCRIPTION OF THE DRAWINGS

FIG. 1. A. Assessment scales used in a test of the dietary supplement. Individuals of the test were asked to answer the questions of the scales and thus to estimate the feeling of hunger/satiety. The upper 2 scales address hunger. The lower scale addresses satiety. The scale goes from −8 to +8 and the questions were answered at different times of the day as illustrated in FIG. 1B. B. Exemplary results obtained in respect of the feeling of hunger/satiety from a test based on ingestion of the dietary supplement. X-axis is the time of the day. 12.30 corresponds to when the products (dietary supplement) was ingested. Hunger is illustrated by a squared figure (grey) and satiety is illustrated by a diamond-shaped figure (black).

FIG. 2. Intake of calories (kCal) with (black) and without (grey) one dose of dietary supplement in connection with lunch. The columns are mean values of 4 days. The dietary supplement was ingested shortly before lunch at 12.30. The intake "before" correspond to caloric intake at breakfast and other food and beverages ingested before lunch. "Lunch" is the amount of calories ingested at lunchtime. "After" is the caloric intake the rest of the day i.e. after ingestion of the lunch. "Total" is the total intake of calories within one day.

FIG. 3. The feeling of hunger/satiety for individuals with and without intake of the dietary supplement. Development of hunger/satiety with (solid lines) and without (dashed lines) intake of dietary supplement in connection with the lunch (just before lunch). 0 on the X-axis represents lunchtime. A: Hunger. B. Satiety. ▲ illustrates hunger without intake of the dietary supplement. ♦ illustrates hunger with intake of the dietary supplement. x illustrates satiety without the intake of the dietary supplement. ■ illustrates satiety with the intake of the dietary supplement.

FIG. 4. Gelation effect of different alginate concentrations. Gelation was scored as:

Absent: 0. A blue color was evenly dispersed in the simulated gastric juice.

Weak: W. A blue color leaked partially into the simulated gastric juice. The alginate was observed as "fluffy" gel pieces with dark blue edges and was thus not a single coherent jet as was observed with strong and intermediate gelation.

Intermediate: I. A blue color leaked partially into the simulated gastric juice. The alginate gel expanded partially and darker colored nodes could be found in the gel. The gel was coherent and the same length as the jet from the pipette.

Strong: S. A blue color was restricted to the alginate. The alginate gel was slightly expanded but maintained the shape of the initial jet from the pipette.

The experiment is further described in example 1B.

EXAMPLES

Example 1A

Gelation Experiments

Materials. The alginates with defined molecular weight, block structure and G-content were obtained from Danisco.

All other chemicals were purchased from Sigma-Aldrich: Anhydrous citric acid (catalogue # C1857), $CaCl_2 \cdot 2H_2O$ (catalogue # C8106), NaCl (catalogue # S3014), Apple pectin (catalogue #76282), guar gum (catalogue # G4129), xylan from beechwood (catalogue # X4252), chitosan from crab shells (catalogue #417963), cellulose, fibrous, medium (catalogue #6288). The alginates from Sigma-Aldrich were low (20-40 cP, 2%), intermediate (approximately 250 cP, 2%) and high (>2000 cP, 2%) viscosity (catalogue # W201502, A2158, A2033 respectively).

Experiments Using Suspended Fibres

In an experiment different fibers were tested for their gelation characteristic. 0.5 g of Na-alginate, pectin, guar gum, xylan, chitosan and cellulose respectively were suspended in 50 ml of pure water.

Water Binding

Suspensions were allowed to stand for 30 minutes at room temperature. Samples were inspected visually for gel formation and for changes in viscosity. In addition the suspensions were filtered and water retention and run through times were recorded.

Pellets/precipitates were observed with Na-alginate, chitosan, pectin and cellulose while no pellets were seen with guar or arabinoxylan.

Viscosity was assessed as the speed of run through. Chitosan and cellulose had run through speeds exceeding 40 ml/min and thus did not increase the viscosity in the suspensions. Na-alginate, pectin and arabinoxylan had an intermediate run through speed around 5-10 ml/min while guar gum rendered the suspension highly viscous with a run through speed lower than 0.5 ml/min.

The amount of water bound was calculated by measuring the volume of filtrate and corrected for the volume of water bound by the filter. Na-alginate and chitosan bound approximately 5 ml of water, pectin and xylan bound around 10 ml of water while cellulose did not bind any water whatsoever. Guar was the only fibre binding considerable amounts of water, as this fibre bound at least 40 ml of water Acid Gelation 0.5 g of Na-alginate, pectin, guar gum, arabinoxylan, chitosan and cellulose respectively were suspended in 50 ml of pure water and allowed to stand for 30 minutes at room temperature. 20 ml of simulated gastric juice (50 mM HCl, 25 mM potassium phosphate (pH 6), 0.25% porcine pepsin) was added to each suspension. Gelation was assessed after 25 minutes at room temperature. Only the guar suspension gelled or became extremely viscous, while alginate, pectin and arabinoxylan turned very turbid and displayed slightly increased viscosity. With chitosan and cellulose no change was observed.

Experiments Using Dissolved Fibres

1% suspensions of alginate, pectin, guar gum and arabinoxylan were heated on a water bath and shaken in order to dissolve the fibres. The solutions were used for gelation experiments.

Dissolution

1% (w/v) suspensions of each of the fibre chitosan, Na-alginate, pectin, guar gum, arabinoxylan in water were heated to just below boiling in a water bath and shaken vigorously. Na-alginate, pectin, arabinoxylan and guar gum dissolved, while cellulose and chitosan remained as suspensions. The solutions were taken for further experiments.

Ca Induced Gels of Alginate 20 ml of a 1% Na-alginate solution was added to 100 ml of 0.003M; 0.006M; 0.0125M; 0.025M; 0.05M; 0.1M 0.25M; 0.5 M; 1.0M $CaCl_2$ respectively. Formation of solid gels was observed with as little as 0.0125M $CaCl_2$ while no gelation was observed with 0.003M $CaCl_2$. A very soft gel was observed with 0.006M $CaCl_2$.

Ca-induced Gels of Varying Alginate Concentrations

Solutions of 0.125%; 0.25% and 0.5% Na-alginate were made. Gelation was tested by adding the solutions to 0.2M $CaCl_2$ and gelation was observed. The experiment was made with 3 different types of Na-alginate: low viscosity, intermediate viscosity and high viscosity. The 3 types all gelled in concentrations down to 0.25%. Intermediate and high viscosity alginate both gelled at 0.125% as well, while the low viscosity alginate did not.

Ca-induced Gels of Chitosan, Cellulose, Pectin, Guar Gum and Arabinoxylan

1% solutions of the above fibres was added to solutions of $CaCl_2$ (concentrations: 0.05M; 0.1M; 0.25M; 0.5M and 1M). None of the fibre solutions formed gels at any $CaCl_2$ concentration tested.

Ca-induced Gels of Pairs of Alginate-fibre Mixtures

Solutions containing 0.5% Na-alginate in combination with 0.5% of either cellulose, chitosan, pectin, guar gum or arabinoxylan were added to solutions of $CaCl_2$ and gelation was observed. $CaCl_2$ concentrations were tested in the range from 0.05M to 0.25M. Gel formation was observed with all combinations except for the combination of alginate/chitosan with 0.05 M $CaCl_2$. Alginate/chitosan and alginate/cellulose formed softer gels than did alginate/pectin; alginate/guar and alginate/arabinoxylan at all $CaCl_2$ koncentrations tested. The firmness of the gels from mixtures of alginate with the soluble fibres were Guar>pectin>arabinoxylan. Pairwise combinations of either cellulose, chitosan, pectin, guar gum and arabinoxylan were tested in a similar way. None of these combinations formed gels.

Ca-induced Gels of Multi-fibre Combinations all Containing Na-alginate

Solutions containing 20% and 25% Na-alginate and 0-50% of cellulose, pectin, guar gum and arabinoxylan were mixed so that the concentration of fibres always was 1% (w/v). The other fibres were added so that individual concentrations were 0, 25, 50% of the total fiber content when 3 additional fibres were included or 0%, 20%, 40% when 4 additional fibres were included. The solutions were tested against 0.1M and 0.25M $CaCl_2$. Gelation was observed for all combinations.

Entrapment of Other Compounds in Ca-induced Alginate Gels

A 1% and a 0.5% solution with added red food coloring was added dropwise to a 0.25M $CaCl_2$ solution. Spherical beads containing the red color was formed immediately without any significant leaking of color. The beads were washed with pure water and then allowed to stand in water for six hours. It was observed that most of the color remained trapped over the observation period. Beads could be flash frozen in liquid nitrogen and freeze dried without any loss of bead integrity.

Gelation of Fibre Solutions and Suspensions in Simulated Gastric Juice

Simulated gastric juice without pepsin (50 mM HCl+25 mM potassium phosphate (pH 6)) was used throughout the experiments.

1% solutions of alginate, pectin, guar gum and arabinoxylan and 1% suspensions of chitosan and cellulose were added to simulated gastric juice and gelation was observed. Only guar gum and alginate formed gels Gelation of Varying Konsentrations of Alginate and Guar Gum in Simulated Gastric Juice Simulated gastric juice without pepsin (50 mM HCl+25 mM potassium phosphate (pH 6)) was used throughout the experiments.

Solutions of guar gum, pectin, arabinoxylan and low, intermediate and high viscosity alginate were tested in concentrations of 0.125%; 0.25%; 0.5% and 1% for gelation when added to simulated gastric juice. Pectin and arabinoxylan did not form gels at any concentration, while guar gum formed gels at 1% but not at any of the lower concentrations. High viscosity alginate formed gels in concentration down to 0.125%, while intermediate and low viscosity alginates formed gels in concentrations down to 0.25%. Retesting high viscosity alginate in a concentration of 0.0625% did not result in formation of gel.

Gelation of Combined Solutions of Alginate and Other Fibres in Simulated Gastric Juice Simulated gastric juice without pepsin (50 mM HCl+25 mM potassium phosphate (pH 6)) was used throughout the experiments. Intermediate and high viscosity alginate in concentrations of 0.5%; 0.25% and 0.125% were tested in pairwise combinations with chitosan, pectin, cellulose, guar gum and arabinoxylans in a concentration of 50%. All combinations with the high viscosity alginate resulted in gel formation. Gelation of intermediate viscosity alginate at 0.125% was prevented in combinations containing chitosan, cellulose or arabinoxylan. An identical observation could be made when simulated gastric juice was replaced with 0.2M $CaCl_2$ Gelation of Redissolved Ca-alginate Gel in Simulated Gastric Juice A 0.25% alginate gel was formed by adding a 0.25% alginate solution to a 0.2M $CaCl_2$ solution. The gel was drained and washed in pure water, made into smaller pieces and a 0.2M solution of citric acid under was added and the mixture was shaken until the gel was partially dissolved. The product was flash frozen in liquid nitrogen and freeze dried. The resulting powder was added to simulated gastric juice and gel formation was observed. The product produced gel fragments with a combined volume slightly smaller than the volume of the original gel.

Conclusions

Products employing fibre-mediated mechanical satiety can be produced by the use of several different strategies:

a) high dose multi or single fibre remedy (dietary supplement):
based on the proven effect of high fibre intake. These types of dietary supplements may be used as pills or as granulates included in standard recipes for hot meals or suspended in drinks. Major drawback is the known side effects of high fibre intake: intestinal pain, gas, diarrhoea, constipation b) low dose alginate based remedy
a. based on the ability of alginate solutions to gel at very low concentrations.
Various other fibres may be included to provide specific physiological or mechanical properties. Other ingredients such as thermogens, chemical satiety inducers, side effect removers and flavours can be included directly in the solutions or provided alongside either as pills/capsules or encapsulated in a small volume of alginate gel. May be used as drink or may be included in various standard food recipes. As the fibre solutions can be made in at least 10% concentration the product can also be provided as a concentrate for mixing with water, milk or other liquids to yield drinks with individually appealing properties b. based on low concentration alginate gels and the ability to redissolve gels in e.g. citric acid. Redissolved gels are freeze dried. The gels may contain additional ingredients such as thermogens, chemical satiety inducers, side effect removers and flavours or these ingredients are provided alongside either as pills/capsules or encapsulated in a small volume of alginate gel. The product may be used as pills or as granulates included in standard recipes for hot meals or suspended in drinks or the product may be included in biscuits or other forms of snacks including crisp bread c. based on low concentration alginate gels. Various other fibres may be included to provide specific physiological or mechanical properties. Other ingredients such as thermogens, chemical satiety inducers, side effect removers and flavours can be included directly in the solutions or provided alongside either as pills/capsules or encapsulated in a small volume of alginate gel. The gels can be used directly as e.g. jellys, puddings, dip for chips or grissini type snacks.

d. based on low concentration alginate gels. Various other fibres may be included to provide specific physiological or mechanical properties. Other ingredients such as thermogens, chemical satiety inducers, side effect removers and flavours can be included directly in the solutions or provided alongside either as pills/capsules or encapsulated in a small volume of alginate gel. The gel can be flash frozen in liquid nitrogen, crushed and freeze dried whereby the spongy nature of the gel is preserved. The product may be used as pills or as granulates included in standard recipes for hot meals or suspended in drinks or the product may be included in biscuits or other forms of snacks including crisp bread High dose, multi-fibre remedy (dietary product)
the high dose remedy relies on "proven" effects of high fibre intake on caloric intake and on physiological/metabolic parameters
a high fibre-dose remedy may be hard to squeeze into a pill format side effects may be gas production in the intestine, intestinal pain, diarrea, constipation can be prepared with remedies with a public appeal Low dose, single or dual fibre remedy low dose remedy (dietary product) relies on the "mechanical satiety" model no side effect easy formulation into pills Example 1B Gelation of Na-alginates A solution of 2% of Na-alginate in distilled water and with blue food colorant added was prepared. Dilutions of this solution were prepared using distilled water containing blue food colorant.

250 μL samples of the above Na-alginate solutions (ranging form 0.0625-1% of alginate) were added to 25 ml of simulated gastric juice (50 mM HCl, 25 mM NaCl). A pipette was used to ad the alginate solution to the simulated gastric juice. Gelation was assessed visually immediately after the addition of the alginate solution to the simulated gastric juice, and was assessed as the ability of the alginate to retain the blue color.

The following table describes some features of the alginate tested:

| Average mw of alginate | Alginate # | G % | GG blocks | MG(GM) blocks | MM blocks |
|---|---|---|---|---|---|
| 50,000 | 1 | 38 | 19 | 39 | 42 |
|  | 2 | 66 | 44 | 46 | 10 |
| 275,000 | 3 | 38 | 19 | 40 | 41 |
|  | 4 | 52 | 32 | 41 | 28 |
| 500,000 | 5 | 37 | 19 | 37 | 44 |
|  | 6 | 62 | 38 | 48 | 13 |

The scoring of the alginate concentrations were as indicted in the following table:

| Alginate # | 0.0625 | 0.1 | 0.125 | 0.2 | 0.25 |
|---|---|---|---|---|---|
| 1 | 0 | w | w | S | S |
| 2 | 0 | w | S | S | S |
| 3 | 0 | I | S | S | S |
| 4 | 0 | I | S | S | S |
| 5 | w | S | S | S | S |
| 6 | 0 | I | S | S | S |

Gelation was scored as absent: 0; weak: w; intermediate: I and strong: s. The scale is described below:

Gelation was scored as (see FIG. 4):

Absent: 0. The blue color was evenly dispersed in the simulated gastric juice.

Weak: W. The blue color leaked partially into the simulated gastric juice. The alginate was observed as "fluffy" gel pieces with dark blue edges and was thus not a single coherent jet as was observed with strong and intermediate gelation.

Intermediate: I. The blue color leaked partially into the simulated gastric juice. The alginate gel expanded partially and darker colored nodes could be found in the gel. The gel was coherent and the same length as the jet from the pipette.

Strong: S. The blue color was restricted to the alginate. The alginate gel was slightly expanded but maintained the shape of the initial jet from the pipette.

In conclusion, alginates in the molecular weight range 50,000-500,000 Dalton were tested for gelation, the frequency of guluronic acid (G) residues varied from 37-68%. Average G-block length varied from 19 G/block (in the alginates with low G %) to 32-44 G/block (in the alginates with high G %). All alginates regardless of molecular weight, G-content and block structure formed acid gels when the concentration was above or equal to 0.1%. The strength of the gel only appeared to depend on molecular weight in concentrations below 0.125%. Thus block structure and G % was not observed to influence acid gelation properties significantly. At the lowest concentration (0.0625%) it even appears that mannuronic acid (M) residues were more willing to gel.

Example 2

Freeze Dried Calcium Gels with all Inclusive

The solution was added to a solution containing 0.1 M $CaCl_2$ and allowed to gel. The gel was washed with distilled water, cut in smaller pieces and frozen quickly in order to avoid syneresis and preserve the spongy structure of the gel. Finally the gel was freeze dried.

A. The product can be formulated into pills or capsules. Each capsule/pill can contain the equivalent of 50-300 ml of gel.

B. The product can be included in snacks or biscuits and e.g. replacing on a dry weight basis an equivalent amount of flour.

C. The product can be included in pasta recipes.

D. the product can be formulated as a noodle/pasta like product

The product can be consumed in connection with the daily meals in order to decrease the caloric intake per meal. In addition the product may be used for in between meals if snacking is the problem for the user.

In all the examples "the equivalent of 50-300 ml gel" represents the dry matter of the amount of gel mentioned. As an example 0.125% of alginate can make a gel in a liquid. Hereby the equivalent of 50-300 ml gel corresponds to 62.5 mg-375 mg of alginate excluding the other compounds of the product. The other compounds of the product may correspond to 0.5 g in total. A 1% of fibre is thus equivalent to 500 mg to 3 g in the pill/capsule when the other active compounds are excluded. Preferably a pill/capsule comprises not more that 1 gram of dry matter in total.

Example 3

Freeze Dried Acid Gels with all Inclusive

A solution containing 0.125-1% Na-alginate, 0-0.5% pectin, 0-0.5% galactomannan, 0-0.5% glucomannan, 0-0.1% cellulose, 0-0.1% chitosan, 700 μL mint oil/L or equivalent dried mint leaves (or equivalent one of the other carminatives), 3-6 mg/L capsaicin or equivalent dried chili powder (or equivalent of one of the other thermogens), 1-100 mg of whey or equivalent protein hydrolysate/L is prepared.

The solution is added to a solution of 0.2M HCl and allowed to gel.

The gel is washed w. distilled water, cut in smaller pieces and frozen quickly in order to avoid synaresis and preserve the spongy structure of the gel. Finally the gel is freeze dried.

A. The product can be formulated into pills or capsules. Each capsule/pill should contain the equivalent of 50-300 ml of gel.
B. The product can be included in snacks or biscuits. Replacing on a dry weight basis an equivalent amount of any suitable ingredient.
C. The product can be included in pasta recipes. Replacing on a dry weight basis an equivalent amount of flour.

Product is to be consumed in connection with the daily meals in order to decrease the caloric intake per meal. In addition the product may be used for in between meals if snacking is the problem for the user.

Example 4

Redissolved Gel—Calcium Induced Gel Titrated w. e.g. Citric Acid Until Dissolved, then Dried A solution containing 0.125-1% Na-alginate, 0-0.5% pectin, 0-0.5% galactomannan, 0-0.5% glucomannan, 0-0.1% cellulose, 0-0.1% chitosan, 700 µL mint oil/L or equivalent dried mint leaves (or equivalent one of the other carminatives), 3-6 mg/L capsaicin or equivalent dried chili powder (or equivalent of one of the other thermogens), 1-100 mg of whey or equivalent protein hydrolysate/L is prepared.

The solution is added to a solution containing 0.1 M CaCl2 and allowed to gel.

The gel is washed w. distilled water, cut in smaller pieces and a solution of citric acid (0.25-0.5 M) is added drop wise under stirring/shaking until the gel is dissolved.

The mixture is dried using spray drying or the mixture is frozen and then freeze dried.

A. The product can be formulated into powder, pills or capsules. Each capsule/pill should contain the equivalent of 50-300 ml of gel.
B. The product can be included in snacks or biscuits. The product may replace on a dry weight basis an equivalent amount of any suitable ingredient or it may be added as an additional ingredient.
C. The product can be included in pasta recipes. The product may replace on a dry weight basis an equivalent amount of any suitable ingredient or it may be added as an additional ingredient.

For the products listed under B and C, the amount of product included in the food product is calculated such that the intake of a given volume of the foodstuff results in occupation of twice that volume in the stomach when contacted with the gastric juice. Product is to be consumed in connection with the daily meals in order to decrease the caloric intake per meal. In addition the product may be used for in-between meals if snacking is the problem for the user.

Example 5

Solubilised Fibre—all Ingredients in

The intended use is as a drink

A solution containing 0.125-1% Na-alginate, 0-0.5% pectin, 0-0.5% galactomannan, 0-0.5% glucomannan, 0-0.1% cellulose, 0-0.1% chitosan, 700 µL mint oil/L or equivalent dried mint leaves (or equivalent one of the other carminatives), 3-6 mg/L capsaicin or equivalent dried chili powder (or equivalent of one of the other thermogens), 1-100 mg of whey or equivalent protein hydrolysate/L is prepared.

A. The product is consumed as a drink (or a "smoothie") directly before a meal
B. The product may have added flavor
C. The product can be added as a "filler" to hot meals
  a. May replace cream
  b. Tomato sauce
  c. other sauces

Example 6

Solubilised Fibre+Protein Lysate—Separate Functional Ingredients

The intended use is as a drink

A solution containing 0.125-1% Na-alginate, 0-0.5% pectin, 0-0.5% galactomannan, 0-0.5% glucomannan, 0-0.1% cellulose, 0-0.1% chitosan and 1-100 mg of whey or equivalent protein hydrolysate/L is prepared. Pills or capsules containing 200 µL mint oil or equivalent dried mint leaves (or equivalent one of the other carminatives), 1-2 mg capsaicin or equivalent dried chili powder (or equivalent of one of the other thermogens) are formulated and swallowed with the fibre solution. Mint oil (or equivalent) and capsaicin (or equivalent) encapsulated in alginate beads formed by making an alginate solution, adding mint oil (or equivalent) and capsaicin (or equivalent) and adding the solution drop wise to a CaCl2 solution. The concentration of mint oil (or equivalent) in the beads should be 100-300 µl/ml and the concentration of capsaicin (or equivalent) should be 1-2 mg/ml. The beads may be dried or used in their hydrated form. The beads are suspended in the drink by shaking immediately before drinking or the beads can be swallowed as pills.

Example 7

Solubilised Fibre+Protein Lysate—Separate Functional Ingredients

The intended use is as a drink

A solution containing 0.125-1% alginate, 0-0.5% pectin, 0-0.5% galactomannan, 0-0.5% glucomannan, 0-0.1% cellulose, 0-0.1% chitosan and 1-100 mg of whey or equivalent protein hydrolysate/L is prepared. Mint oil (or equivalent) and capsaicin (or equivalent) encapsulated in alginate beads formed by making an alginate solution, adding mint oil (or equivalent) and capsaicin (or equivalent) and adding the solution drop wise to a CaCl2 solution. The concentration of mint oil (or equivalent) in the beads should be 100-300 µl/ml and the concentration of capsaicin (or equivalent) should be 1-2 mg/ml. The beads may be dried or used in their hydrated form. The beads are suspended in the drink by shaking immediately before drinking or swallowed as pills.

Example 8

Concentrated Solubilised Fibre

The fibre containing solutions from examples 4, 5 and 6 may be prepared in concentrated form (e.g. 10-100× concentrated) and diluted with water to the desired concentration just before drinking.

A. The concentrates together with encapsulated carminative and thermogen may be provided with ready to heat convenience food or with recipes for specialized low calorie food.
B. The concentrates together with encapsulated carminative and thermogen may be provided with or in a dedicated shaker where only water or other liquid has to be added.

Example 9

Fibre Gel Containing all Ingredients

A solution containing 0.125-1% Na-alginate, 0-0.5% pectin, 0-0.5% galactomannan, 0-0.5% glucomannan, 0-0.1% cellulose, 0-0.1% chitosan, 700 µL mint oil/L or equivalent dried mint leaves (or equivalent one of the other carminatives), 3-6 mg/L capsaicin or equivalent dried chili powder (or equivalent of one of the other thermogens), 1-100 mg of whey or equivalent protein hydrolysate/L is prepared. Any flavors may be added before gelation or the carminative is selected for flavor.

The solution is added to a solution containing 0.1 M $CaCl_2$ and allowed to gel.

A. The gel may be eaten with a spoon
B. The gel may be part of a snack and be eaten with e.g. grissini like sticks. Mint oil (or equivalent) and/or capsaicin (or equivalent) may be included with the grissini like sticks.
C. The gel may be used as jelly on low calorie bread
D. The gel may be sandwiched between two pieces of crispbread as a ready-to-eat snack

Example 10

Fibre Gel with Encapsulated Carminatives and Thermogens

A solution containing 0.125-1% Na-alginate, 0-0.5% pectin, 0-0.5% galactomannan, 0-0.5% glucomannan, 0-0.1% cellulose, 0-0.1% chitosan and 1-100 mg of whey or equivalent protein hydrolysate/L is prepared. Beads containing carminative and thermogen (Mint oil (or equivalent) and capsaicin (or equivalent) encapsulated in alginate beads formed by making an alginate solution, adding mint oil (or equivalent) and capsaicin (or equivalent) and adding the solution drop wise to a $CaCl_2$ solution. The concentration of mint oil (or equivalent) in the beads should be 100-300 µl/ml and the concentration of capsaicin (or equivalent) should be 1-2 mg/ml. The beads may be dried or used in their hydrated form.) The beads are added to the solution. The solution is added to a solution of citric acid and allowed to gel. Any flavors may be added before gelation or the carminative is selected for flavor.

A. The gel may be eaten with a spoon
B. The gel may be part of a snack and be eaten with e.g. grissini like sticks. Mint oil (or equivalent) and/or capsaicin (or equivalent) may be included with the grissini like sticks.
C. The gel may be used as jelly on low calorie bread
D. The gel may be sandwiched between two pieces of crispbread as a ready-to-eat snack

Example 11

Dry Fibres

Fibres are weighted and portioned. Whey or protein hydrolysate are weighted and portioned. Beads containing carminative and thermogen are prepared (Mint oil (or equivalent) and capsaicin (or equivalent) encapsulated in alginate beads formed by making a Na-alginate solution, adding mint oil (or equivalent) and capsaicin (or equivalent) and adding the solution drop wise to a $CaCl_2$ solution. The concentration of mint oil (or equivalent) in the beads should be 100-300 µl/ml and the concentration of capsaicin (or equivalent) should be 1-2 mg/ml) and dried and portioned together with fibre and whey/protein hydrolysate.

The product may be used to lower the caloric density and providing thermogen and carminative effect to any liquid meal or any liquid meal element.

Example 12

Appetite Reducing Remedy—Recipe and Use

The remedy is intended to reduce the caloric intake/food consumption per meal and is preferably to be ingested 5-30 minutes before one or more meals each day, such as ingested 5-30 minutes before each meal (e.g. before breakfast, lunch and dinner).

Composition/dose may be:
- 0.375-1.5 g of fibre e.g. of alginate corresponding to 0.125-0.5% (v/w) alginate in the final solution which is to be ingested,
- 1-100 mg of whey or legume protein hydrolysates,
- Optionally dried chilli, pepper or ginger corresponding to 2 mg vannilloid (e.g. capsaicin, piperin, gingerol or derivatives), and
- 200 µl of mint oil, or dried mint leaves corresponding to 200 µl of mint oil This dose is intended to be dissolved in approximately 300 of liquid such as water before ingestion.

Fibres can be glucomannan, galactomannan, alginate, pectin, cellulose, chitosan, gellan gum. Preferred is a fibre of glucomannan, galactomannan, alginate, pectin, or the fibres may be a combination of the mentioned fibre. Up to about 10% of the fibres can be cellulose or chitosan in order to improve rehydration properties.

Whey may be obtained from bovine, ovine or caprine sources. Preparation of the whey, and selection of the source can be used to increase/manipulate the amount/quality of the active principle (GMP).

The active principle in plant (e.g. soy, potato) protein hydrolysates are proteinase inhibitors (e.g. soybean trypsin inhibitor and/or PI2 from potato). The content/quality of inhibitor can be manipulated by source and preparation Chilli may be *Capsicum frutescens*, but non-pungent cultivars of *Capsicum annuum* may be used as an alternative, as may any member of the genus *Capsicum*.

Pepper may be *Piper nigrum*, but other members of the genus (e.g. *Piper cubeba, Piper longum, Piper umbellatum*) may be used. Members of other genera (e.g. *Anethum graveolens, Habzelia aethiopcia*) may also be used Mint oil means oil prepared from the leaves of *Mentha piperita*, but several members (possibly all) of the genus *Mentha* may be used as well.

A number of herbs can be used as thermogens and/or side effect remover. Chilli, pepper and ginger as mentioned above may be substituted by any other thermogen plant or compound mentioned herein. Mint oil may be substituted by any extract e.g. oil extract or plant part described herein as a side effect remover.

Example 13

Test of Appetite Reducing Formulation

A dietary supplement according to the description herein has been tested with human individuals.

Formulation:
600 mg Na-alginate and 100 mg whey was dissolved in 300 ml of water. Powdered chili corresponding to 2.5 mg capsaicin and 200 μl mint oil were encapsulated in 1.5 ml of freeze dried Ca-alginate beads. One dose consisted of the amount just described.

Administration

The preparation was taken 5-10 min. before lunch. The beads containing the chilli and mint oil were swallowed during drinking of the alginate/whey solution. After ingestion of the preparation individuals were allowed to eat unrestricted.

Experimental

Two adult individuals—one female and one male of normal weight took one daily dose in connection with lunch for a period of 4 days. The two subjects registered satiety/hunger and caloric intake for these 4 days and for 4 days when not ingesting the product.

Scoring of Results

For scoring of the results relating to hunger/satiety a 16 cm visual assessment scale was used when the dairy supplement was ingested. Two different questions were asked for assessment of hunger while one scale was used for assessment of satiety.

The questions were:
"How hungry are you?" and the answers could be answered anywhere on the 16 cm assessment scale ranging from "not at all" (−8) to "like a wolf" (8).
"How much could you eat?" and the answers could be answered anywhere on the 16 cm assessment scale ranging from "absolutely nothing" (−8) to "empty the fridge" (8).
"How satiated do you feel?" and the answers could be answered anywhere on the 16 cm assessment scale ranging from "not at all" (−8) to "extremely" (8).

In FIG. 1 part A) indicates the assessment scales, the questions and the possible answers. Part B) of FIG. 1 shows exemplary answers of an individual ingesting the diary supplement just before lunch. The figure illustrates the symmetrical values of satiety/hunger ratings when the described visual assessment scales are used. One graph indicates "satiety", the other graph indicates "hunger" and these are correlated to the time of day indicated by the hour of the X-axis. At 12.30 the dietary supplement was ingested.

Caloric intake: The individuals were asked to fill in an eating diary listing any intake and the time when the food/drink was ingested. The caloric content of the ingested food was calculated on the basis of weight and caloric content available from publicly available data.

Side effects: The individuals were also asked to report any side effects/odd sensations.

Results

The results obtained in the test of the dietary supplement can be summarised as:
1. No gender difference in response to the dietary supplement.
2. No side effects reported.
3. The formulation resulted in a lower caloric intake of about 30% on the days when the dietary supplement was ingested relative to the days with no intake of the product. This reflected a 40% decrease in lunch intake and a 50% decrease in food intake after lunch and including dinner i.e. for the rest of the day following lunch time. FIG. 2 indicates the intake of calories with (black) and without (grey) ingestion of one dose of the dietary supplement in connection with lunch. "Before" indicates calories ingested before lunch. "Lunch" indicates calories ingested at lunch i.e. shortly after ingestion of the dietary supplement. "After" indicates calories ingested after lunch i.e. for the rest of the day. "Total" indicates the total intake of calories. Mean number of four days.
4. Hunger/satiety ratings were visually assessed and both showed a doubling in the time after lunch in which the individuals felt satiated, and inversely a doubling in time before hunger set in after lunch when the dietary supplement was ingested. FIG. 3 shows the changes in the feeling of hunger (part A) and satiety (part B) with (solid lines) and without (dahed lines) ingestion of the dietary supplement shortly before lunch time.

Exemplary recipes containing different formulations of the weight control remedy 1) Dried redissolved Ca-alginate gel with whey protein. Dry gel encapsulated thermogen and side effect remover Chocolate chip cookies:

Ingredients for 24 cookies:

180 g flour
1 teaspoon baking powder
1 teaspoon salt
150 g butter
180 g sugar
120 g brown sugar
1 tea spoon vanilla sugar
2 eggs
300 g chocolate chips
100 chopped hazel nuts After the ingredients are mixed is added 26.2 g of dried re-dissolved Ca-alginate gel (1.25 g Na-alginate, 5.55 g $CaCl_2$, 19.2 g citric acid), containing 100 mg whey protein. Further is added 3 g chilli powder and 1.6 ml of mint oil encapsulated in 0.2% Ca-alginate dried pellets (1-2 mm).

2) Dried redissolved Ca-alginate gel with whey protein. Dry gel encapsulated thermogen and side effect remover Wheat biscuits Ingredients for 50 biscuits:

125 g butter
50 g sugar
½ teaspoon salt
1 teaspoon baking powder
300 g wheat flour
150 ml cream After the ingredients are mixed is added 26.2 g of dried re-dissolved Ca-alginate gel (1.25 g Na-alginate, 5.55 g $CaCl_2$, 19.2 g citric acid), containing 100 mg whey protein. Further is added 3 g chilli powder and 1.6 ml of mint oil encapsulated in 0.2% Ca-alginate dried pellets (1-2 mm).

3) Dried redissolved Ca-alginate gel with whey protein. Dry gel encapsulated thermogen and side effect remover Muffins Ingredients for 12 muffins 175 ml oil
1 teaspoon vanilla sugar
100 g brown sugar
2 eggs
100 g walnuts lightly chopped
200 g apples
2 teaspoons powdered ginger
1 teaspoon powdered cinnamon
½ teaspoon baking powder
1 teaspoon soda After the ingredients are mixed is added 52 g of dried re-dissolved Ca-alginate gel (2.5 g Na-alginate 11.1 g $CaCl_2$, 38.4 g citric acid), containing 100 mg whey protein. Further is added dried pellets of Ca-alginate (1-2 mm) containing 6 g chilli powder and 3.2 ml of mint oil.

Soups
4) Native Na-alginate+whey. Dried Ca-alginate gel or dried acid-Na-alginate gel. Native thermogen and side effect remover
Chicken soup:
100 g noodles
1.5 L chicken broth
3 shallots
6 slices of ginger
2 tablespoons fish sauce
300 g boiled chicken After the soup has boiled for c. 8 minutes 2 g of Na-alginate and 200 mg of whey protein is added and the soup is stirred until the alginate has dissolved.

Further caloric reduction can be obtained by replacing the noodles with noodles made of Ca-alginate gel or of acid induced Na-alginate gel. (e.g. example 3), further is added 200 mg of whey protein.
garnish:
Adzuki sprouts
Fresh mint leaves
Freshly chopped chilli The above garnish adds systemic satiety inducer, thermogen and side effect remover to the meal.
Dragon soup
5) Native Na-alginate+whey. Dried gel encapsulated thermogen and side effect remover.
½ kg chicken breast
2 L chicken broth
Salt & pepper
4 carrots
½ celery
Parsley
2 leeks 2 minutes before the soup is ready is added 2.5 g of Na-alginate and 200 mg of whey protein. Just before serving is added dried pellets of Ca-alginate (1-2 mm). containing 6 g chilli powder and 3.2 ml of mint oil.

Can be served with wholemeal buns:
5a) Dried redissolved Ca-alginate gel with whey protein. Dry gel encapsulated thermogen and side effect remover
For 10 buns:
200 ml water
100 g whole wheat
25 g bakers yeast
200 ml yogurt
1 teaspoon honey
100 g Wholemeal flour
475 g wheat flour After the ingredients are mixed is added 52. g of dried re-dissolved Ca-alginate gel (2.5 g Na-alginate 11.1 g CaCl$_2$, 38.4 g citric acid), containing 100 mg whey protein. Further is added dried pellets of Ca-alginate (1-2 mm). containing 6 g chilli powder and 3.2 ml of mint oil.
Tomato soup
6) Native Na-alginate+whey. Native side effect remover. Native side effect remover (thyme+oregano)
Olive oil
2 onions
1 tablespoon oregano
1 tablespoon thyme
2 loafs of garlic
800 g tomatoes
300 ml water
2½ tablespoon tomato paste
2 teaspoons sugar
Salt & pepper When the soup is otherwise ready to eat 2 g of Na-alginate and 200 mg of whey protein is added and the soup is stirred until the alginate has dissolved. Further is added dried pellets of Ca-alginate (1-2 mm). containing 6 g chilli powder. Side effect remover is provided by the oregano and the thyme in the recipe.
Meat balls (10)
7) Dried redissolved Ca-alginate gel with whey protein. Native thermogen and side effect remover
400 g minced meat
1 loaf pressed garlic
A handful of chopped mint leaves
1 egg
½ teaspoon powdered cumin
½ teaspoon powdered coriander
Cayenne powder After the ingredients are mixed is added 52. g of dried re-dissolved Ca-alginate gel (2.5 g Na-alginate 11.1 g CaCl$_2$, 38.4 g citric acid), containing 100 mg whey protein. Thermogen and side effect remover are provided by cayenne and the mint leaves.
Dumplings in curry (20 dumplings)
8) Dried redissolved Ca-alginate gel with whey protein. Native thermogen and side effect remover. Native Na-alginate+whey. Dried Ca-alginate gel or dried acid-Na-alginate gel Same recipe as for meat balls above
Curry sauce:
20 g butter
½ cup chopped onions
2 teaspoons of curry (or more)
1 apple
2½ tablespoon of flour
600 ml water from the boiled dumplings When the sauce is ready add 1 g of Na-alginate plus 200 mg of whey protein and stir until dissolved.

Serve with rice or with Ca-alginate noodles
Snacks
9)) Dried redissolved Ca-alginate gel with whey protein. Dry gel encapsulated thermogen and side effect remover
Grissini (14)
250 g flour
25 g bakers yeast
2 tablespoon oil
½ teaspoon honey
125 ml water After the ingredients are mixed is added 26.2 g of dried re-dissolved Ca-alginate gel (1.25 g Na-alginate, 5.55 g CaCl$_2$, 19.2 g citric acid), containing 100 mg whey protein. Further is added 3 g chilli powder and 1.6 ml of mint oil encapsulated in 0.2% Ca-alginate dried pellets (1-2 mm).

The grissini can be eaten with e.g. salsa:
9a) Concentrated Na-alginate solution.
Strawberry salsa:
250 g chopped strawberries
2 tablespoons onions
2 tablespoons rose jelly
2 tablespoons lemon juice
1 chopped chilli
1 tablespoon honey
3 tablespoons Lemon balm
Salt
10 ml of a 5% Na-alginate solution
Traditional salsa:
1 can peeled tomatoes
2 chilies
1 teaspoon coriander Lemon juice (1 lemon)
1 loaf of pressed garlic
12 ml of a 5% Na-alginate solution
salt
Vanilla Ice
10) Concentrated Na-alginate solution. Native whey. Dry gel encapsulated thermogen and side effect remover
500 ml whipped cream
5 egg yolks
75 g sugar
Vanilla grains from 1 pod
3-4 salt grains Whip egg yolks+ sugar+ vanilla grains, before mixing all ingredients After mixing add 20 ml of a 5% Na-alginate solution+500 mg of whey protein.

Pour into ice machine and add 50 g of chopped dark chocolate and 1 g chilli powder and 0.5 ml of mint oil encapsulated in 0.2% Ca-alginate dried pellets (1-2 mm).

The invention claimed is:

1. A dietary supplement for treating obesity in a human in need thereof consisting essentially of therapeutically effective amounts of alginate, *Capsicum frutescens* extract, *Mentha piperita* extract and glucomacropeptide.

2. The dietary supplement of claim 1, wherein the amount of the glucomacropeptide in a dose of said supplement is in the range of 0.1 mg to 100 mg.

3. The dietary supplement of claim 1, wherein the amount of the *Mentha piperata* extract in a dose of said supplement is in the range of 0.1 mg to 100 mg.

4. The dietary supplement of claim 1, wherein the amount of the *Capsicum frutescens* extract in a dose of said supplement is in the range of 0.1 mg to 100 mg.

5. The dietary supplement of claim 1, wherein the amount of alginate in a dose of said supplement is in the range of 100-1500 mg.

6. The dietary supplement of claim 1, wherein the dietary supplement is in a form selected from the group consisting of a powder, a pill, a tablet, a capsule, a gel, and a liquid.

7. A method of regulating the appetite in a human or an animal, consisting essentially of administering the dietary supplement of claim 1 to said human or animal.

* * * * *